(12) United States Patent
Daliri Rezagholi Gheshlaghi et al.

(10) Patent No.: US 10,556,049 B2
(45) Date of Patent: Feb. 11, 2020

(54) TWISTING BIVENTRICULAR CARDIAC ASSIST DEVICE

(71) Applicants: Mahdi Daliri Rezagholi Gheshlaghi, Tehran (IR); Seyed Javad Hosseini Hooshyar, Tehran (IR); Mona Yadollahi, Tehran (IR)

(72) Inventors: Mahdi Daliri Rezagholi Gheshlaghi, Tehran (IR); Seyed Javad Hosseini Hooshyar, Tehran (IR); Mona Yadollahi, Tehran (IR)

( * ) Notice: Subject to any disclaimer, the term of this patent is extended or adjusted under 35 U.S.C. 154(b) by 0 days.

(21) Appl. No.: 16/155,138

(22) Filed: Oct. 9, 2018

(65) Prior Publication Data
US 2019/0070346 A1 Mar. 7, 2019

Related U.S. Application Data

(63) Continuation-in-part of application No. PCT/IB2018/050001, filed on Jan. 1, 2018, and a continuation-in-part of application No. PCT/IB2017/051532, filed on Mar. 16, 2017.

(51) Int. Cl.
*A61M 1/10* (2006.01)
*A61M 1/12* (2006.01)
*A61B 18/00* (2006.01)
*A61B 17/00* (2006.01)

(52) U.S. Cl.
CPC .......... *A61M 1/1044* (2014.02); *A61M 1/106* (2013.01); *A61M 1/122* (2014.02); *A61B 2017/00243* (2013.01); *A61B 2018/00351* (2013.01); *A61M 1/107* (2013.01); *A61M 1/1086* (2013.01); *A61M 2205/3303* (2013.01); *A61M 2205/3331* (2013.01)

(58) Field of Classification Search
USPC ...................................... 600/16–18, 300–301
See application file for complete search history.

(56) References Cited

U.S. PATENT DOCUMENTS

| 6,146,114 | A  | * | 11/2000 | Nardacci  | .................... | F41F 3/10 |
| | | | | | | 417/437 |
| 6,602,182 | B1 | * | 8/2003 | Milbocker | ............ | A61M 1/106 |
| | | | | | | 600/16 |
| 7,883,325 | B2 | * | 2/2011 | Kheradvar | ............ | F04B 43/046 |
| | | | | | | 417/472 |
| 9,656,009 | B2 | * | 5/2017 | Kheradvar | .......... | A61M 1/1068 |
| 10,035,020 | B2 | * | 7/2018 | Wang | .................... | A61N 1/0551 |

(Continued)

*Primary Examiner* — Niketa I Patel
*Assistant Examiner* — Shirley X Jian
(74) *Attorney, Agent, or Firm* — Summit Patent Group

(57) ABSTRACT

A cardiac assist device is provided. The cardiac assist device may comprise a structure surrounding at least a portion of a heart. The cardiac assist device may comprise an inner cup enclosing at least a portion of the structure. The cardiac assist device may comprise an outer cup enclosing at least a portion of the inner cup. The outer cup may comprise an opening. Gas may be conducted into a space between the outer cup and the inner cup, using a pump, to cause a first motion of the structure, associated with a first rotation of a first portion of the heart in a first direction. The gas may be conducted from the space to outside of the outer cup, using the pump, to cause a second motion of the structure, associated with a second rotation of the first portion of the heart in a second direction.

16 Claims, 15 Drawing Sheets

(56) References Cited

U.S. PATENT DOCUMENTS

| | | | |
|---|---|---|---|
| 10,058,647 B2* | 8/2018 | Roche | F15B 15/103 |
| 10,130,456 B2* | 11/2018 | Wildhirt | A61F 2/0063 |
| 2002/0007216 A1* | 1/2002 | Melvin | A61F 2/02 |
| | | | 623/3.11 |
| 2004/0097787 A1* | 5/2004 | French | A61F 2/2481 |
| | | | 600/37 |
| 2004/0167375 A1* | 8/2004 | Couvillon, Jr. | A61M 1/1068 |
| | | | 600/17 |
| 2004/0225177 A1* | 11/2004 | Coleman | A61M 1/107 |
| | | | 600/17 |
| 2004/0267086 A1* | 12/2004 | Anstadt | A61M 1/1068 |
| | | | 600/17 |
| 2006/0142634 A1* | 6/2006 | Anstadt | A61M 1/1068 |
| | | | 600/16 |
| 2006/0167334 A1* | 7/2006 | Anstadt | A61M 1/106 |
| | | | 600/17 |
| 2006/0216173 A1* | 9/2006 | Kheradvar | F04B 43/046 |
| | | | 417/478 |
| 2007/0021646 A1* | 1/2007 | Nardi | A61M 1/106 |
| | | | 600/16 |
| 2008/0033228 A1* | 2/2008 | Rastegar | A61H 9/0078 |
| | | | 600/16 |
| 2012/0010455 A1* | 1/2012 | Reichenbach | A61M 1/10 |
| | | | 600/16 |
| 2016/0346449 A1* | 12/2016 | Roche | F15B 15/103 |
| 2019/0060542 A1* | 2/2019 | Altman | A61M 1/122 |

* cited by examiner

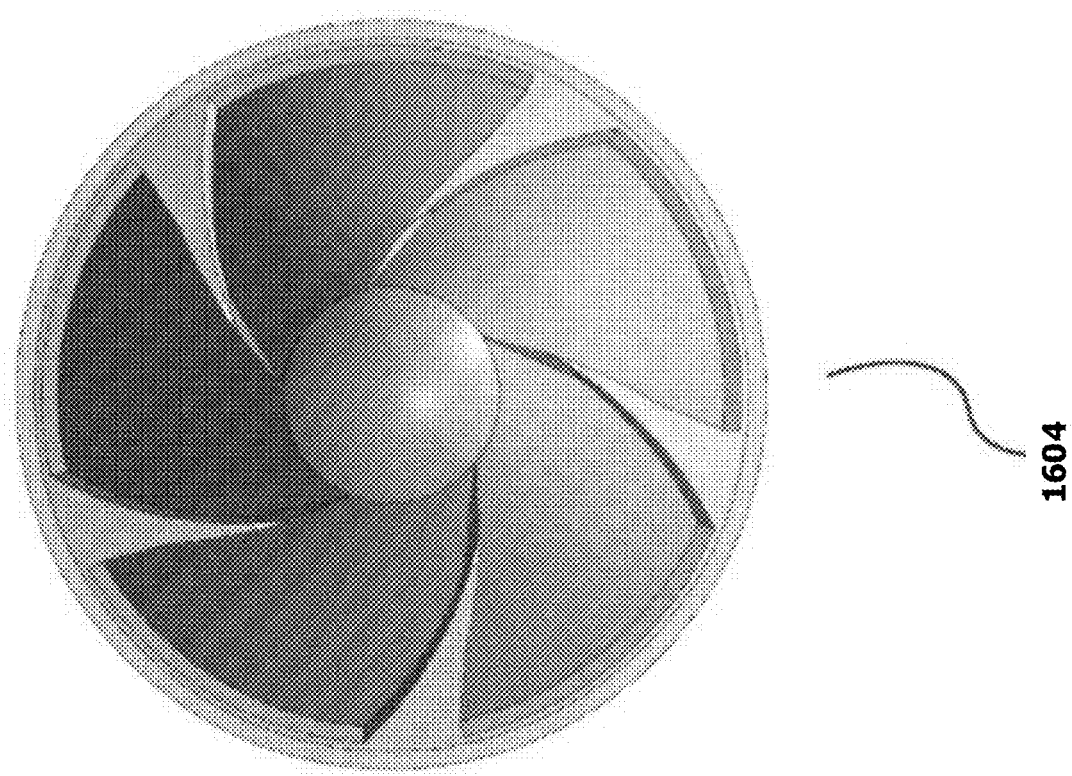
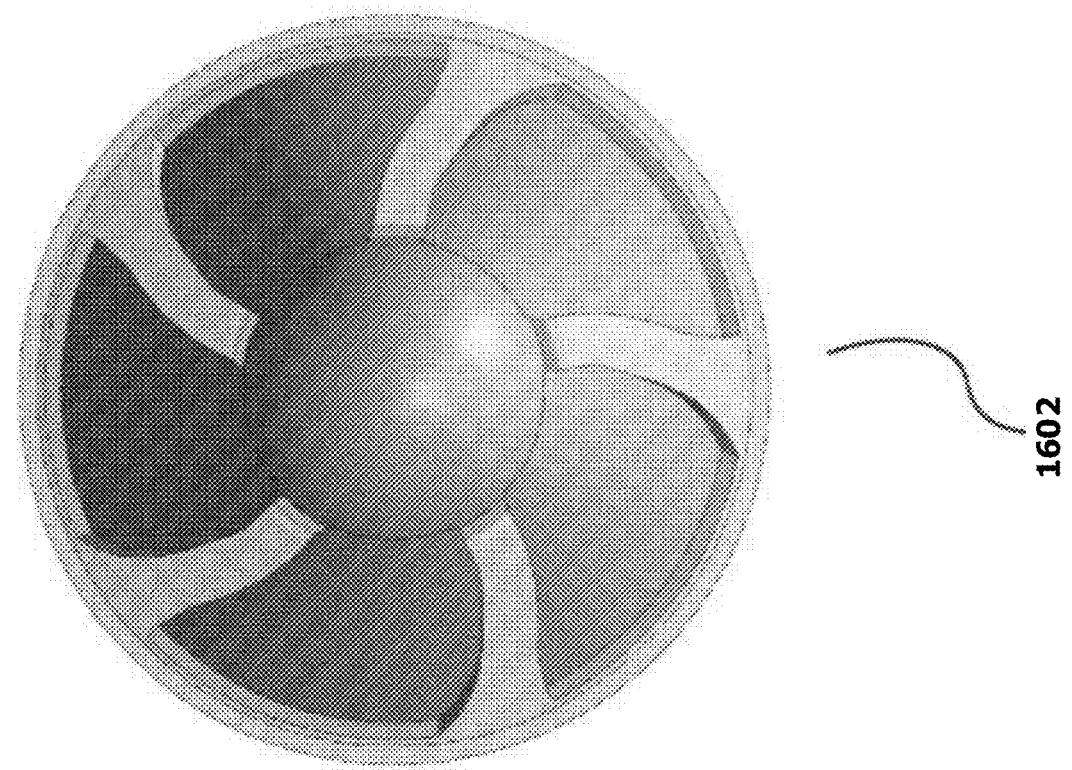
FIG. 16

TWISTING BIVENTRICULAR CARDIAC ASSIST DEVICE

RELATED APPLICATIONS

This is a continuation-in-part of International Application PCT/IB2017/051532, which was filed on Mar. 16, 2017, and which claims priority to Iran Patent No. 90030 of Iran Application Number 139550140003000583, which was filed on Apr. 10, 2016. This is a continuation-in-part of International Application PCT/IB2018/050001, which was filed on Jan. 1, 2018. International Application PCT/IB2017/051532 and International Application PCT/IB2018/050001 are incorporated herein by reference.

BACKGROUND

Cardiac assist devices, such as ventricular assist devices (VADs), left ventricular assist devices (LVADs), biventricular assist devices (BIVADs), etc. may be used to support heart function and blood flow in people with weakened hearts. For example, cardiac assist devices may be used as short-term solutions (e.g., during and/or after surgery, during recovery, while waiting for a heart transplant, etc.). Alternatively and/or additionally, cardiac assist devices may be used as long-term solutions to support heart function. Further, cardiac assist devices may have limited resources and/or may have limited capabilities.

SUMMARY

This summary is provided to introduce a selection of concepts in a simplified form that are further described below in the detailed description. This summary is not intended to identify key factors or essential features of the claimed subject matter, nor is it intended to be used to limit the scope of the claimed subject matter.

In an example, a cardiac assist device is provided. The cardiac assist device may comprise a structure surrounding at least a portion of a heart. The structure may comprise a first ring on a first side of the structure (e.g., the first ring may be positioned around the heart), a second ring on a second side of the structure (e.g., the second ring may be adjacent to a bottom of the heart) and/or a plurality of columns connecting the first ring to the second ring. The structure may comprise an inner cup enclosing at least a portion of the structure. Alternatively and/or additionally, the structure may comprise an outer cup enclosing at least a portion of the inner cup. The outer cup may comprise an opening. At a first instance, gas may be conducted via the opening into a space between the outer cup and the inner cup. The gas may be conducted into the space using a pump. The gas being conducted into the space may cause a first motion of the structure. The first motion may be associated with a first rotation of the second ring in a first direction. At a second instance, the gas is conducted via the opening from the space to outside of the outer cup, using the pump. The gas being conducted from the space to the outside of the outer cup causes a second motion of the structure. The second motion may be associated with a second rotation of the second ring in a second direction, different than the first direction.

In an example, a cardiac assist device is provided. The cardiac assist device may comprise a structure surrounding at least a portion of a heart. The structure may comprise a first ring on a first side of the structure, a second ring on a second side of the structure and/or a plurality of columns connecting the first ring to the second ring. The structure may comprise a cup enclosing at least a portion of the structure. The structure may comprise a motor configured to rotate the second ring in a first direction at a first instance, and/or rotate the second ring in a second direction at a second instance. The second direction may be different than the first direction.

In an example, a cardiac assist device is provided. The cardiac assist device may comprise a cup enclosing at least a portion of a heart. The cup may comprise an inner layer and an outer layer. The outer layer of the cup may comprise an opening. At a first instance, gas may be conducted via the opening into a space between the outer layer and the inner layer. The gas may be conducted into the space using a pump. The gas being conducted into the space may cause a first motion of the inner layer. The first motion may be associated with a first rotation of a first portion of the heart in a first direction. At a second instance, the gas is conducted via the opening from the space to outside of the outer layer, using the pump. The gas being conducted from the space to the outside of the outer layer causes a second motion of the inner layer. The second motion may be associated with a second rotation of the first portion of the heart in a second direction, different than the first direction.

DESCRIPTION OF THE DRAWINGS

While the techniques presented herein may be embodied in alternative forms, the particular embodiments illustrated in the drawings are only a few examples that are supplemental of the description provided herein. These embodiments are not to be interpreted in a limiting manner, such as limiting the claims appended hereto.

FIG. 16 is a drawing illustrating an exemplary second cardiac assist device.

DETAILED DESCRIPTION

Figure 1:
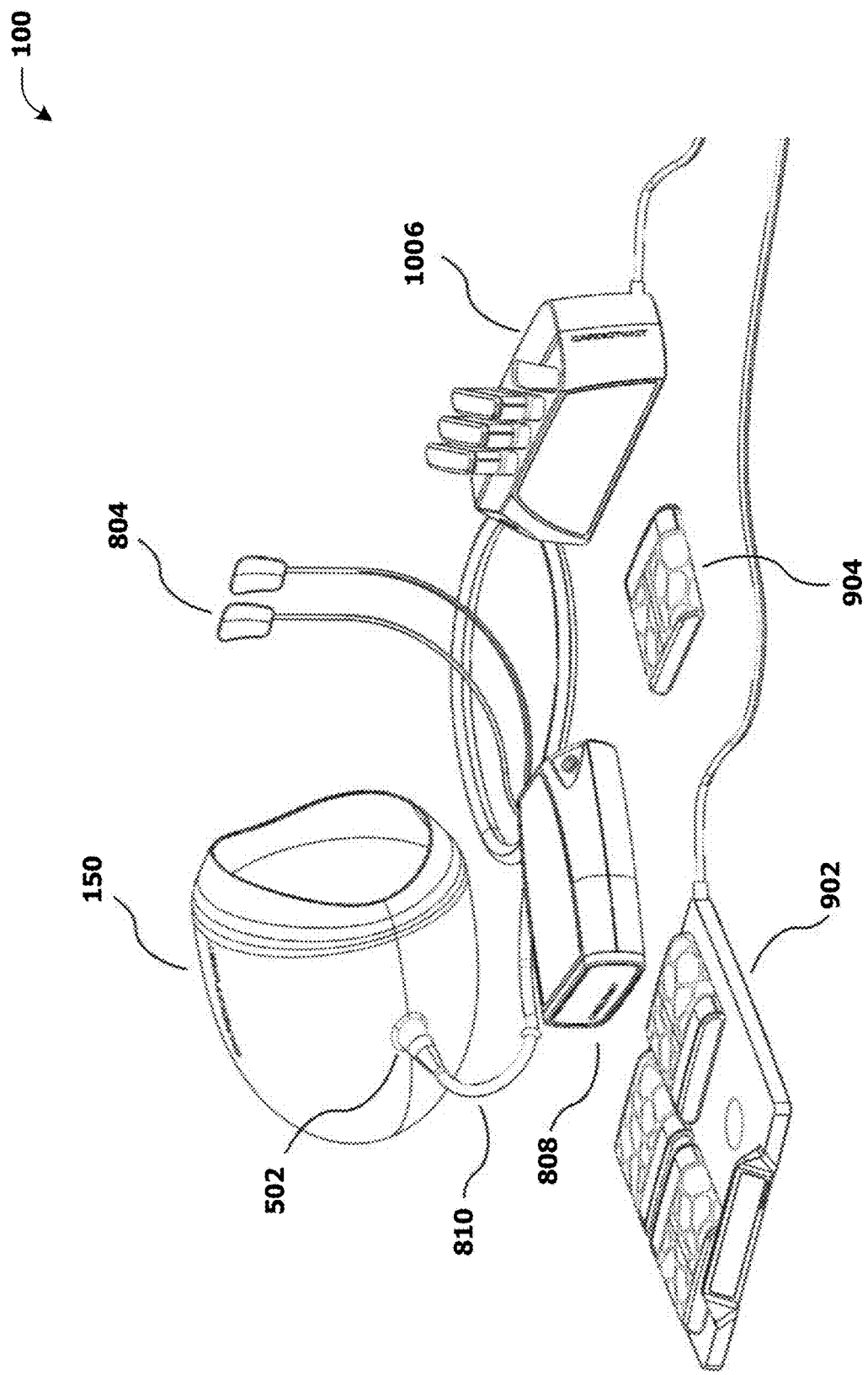
FIG. 1 is a component block diagram illustrating an exemplary cardiac assist device.

Subject matter will now be described more fully herein after with reference to the accompanying drawings, which form a part hereof, and which show, by way of illustration, specific example embodiments. This description is not intended as an extensive or detailed discussion of known concepts. Details that are known generally to those of ordinary skill in the relevant art may have been omitted, or may be handled in summary fashion.

The following subject matter may be embodied in a variety of different forms, such as methods, devices, components, and/or systems. Accordingly, this subject matter is not intended to be construed as limited to any example embodiments set forth herein. Rather, example embodiments are provided merely to be illustrative. Such embodiments may, for example, take the form of mechanical devices, electro-mechanical devices, electrical devices, biomechanical devices, bioelectrical devices, or any combination thereof.

Many cardiac assist devices in existing technology, such as ventricular assist devices (VADs), left ventricular assist devices (LVADs), biventricular assist devices (BIVADs), etc. may expose a patient to potentially serious complications. A main cause of complications is direct contact of the patient's circulation to artificial surfaces as well as invasive surgical procedures. Hemorrhage is a common complication associated with placement of LVAD. Excessive perioperative bleeding occurs between 20% and 50% of the time; however, this rate decreases as experience with device implantation grows. About 50% of patients required reoperation for bleeding, while death due to bleeding was reported to be in the range of 0 to 15%. Infection is another serious complication and the primary cause of death in long-term LVAD patients. The mortality is up to 70% of LVAD recipients. Failure of the LVAD was the second most frequent cause of death in the device group, which can occur in multiple parts of a device or in the controller.

With advancements of existing technology, pumping mechanical failure has decreased (0.03% in 1th generation to 0% in 2nd and 3rd generation of LVAD). Right heart failure (RHF) is also a common complication associated with VADs, occurring in nearly 40% of recipients. RHF is also associated with high transfusion rate and increased rate of end-organ failure. The number of days in the intensive care unit and the mortality rate are also increased in RHF patients. Thromboembolism is a significant complication that occurs in 20% of patients receiving left or right VADs. The main cause of thromboembolism is contact of device surface to blood and this event depends on many factors like device profile, patient condition and anticoagulant regimen. This may be due to cerebrovascular and peripheral embolization. Other less common complications are ventricular arrhythmias, stroke, neurological and psychological dysfunction, hemolysis and/or other organs dysfunction.

Further, extra-cardiac compression devices (ECCDs) may require major surgery, such as a thoracotomy and/or a sternotomy, for implantation of an ECCD. Use of ECCDs in earlier stage patients is thus restricted and it may be beneficial to use the ECCDs merely for long-term applications due to the invasiveness. A large size and complex mechanism of an ECCD makes the surgical procedure as well as the intracorporeal fixation challenging. Size and weight of the device is a critical issue in smaller patients. Other significant risks for direct compression devices are adhesion and tissue ingrowth. Cardiac recovery has been reported after mechanical assistance by VADs allowing the removal of the device. If this remodeling process would be expected, besides the invasive surgery required to withdrawal the ECCD, device removal could result in substantial damage to the cardiac or vessel muscles due to tissue adhesion or ingrowth. Another situation in which a device removal is necessary is body rejection. Despite elimination or minimization of the direct blood contact in the ECCDs, the adjacency between artificial surfaces and internal organs are not avoidable. Further investigation on potential immune system activation due to the ECCDs is necessary before they are proven beneficial or capable of being alternatives to current VADs.

Thus, further development of cardiac assist devices may be beneficial in developing a cardiac assist device that may be an alternative to heart transplantation such that a reliability and/or a longevity of the cardiac assist device advances towards that of a heart transplant.

FIG. 1 presents a cardiac assist device 100. For example, the cardiac assist device 100 may comprise a set of cups 150 (e.g., a set of one or more cups), a controller 808 (e.g., further illustrated in FIG. 8), one or more electrocardiogram leads 804 (e.g., further illustrated in FIG. 8), a first battery charger 902 (e.g., further illustrated in FIG. 9) and/or a second battery charger 1006 (e.g., further illustrated in FIG. 10). The controller 808 may comprise a pump configured to conduct gas and/or liquid into the set of cups 150 via a first part of a cannula 810 (e.g., further illustrated in FIG. 8) and/or a second part of the cannula 502 (e.g., further illustrated in FIG. 5). For example, the pump may be a pneumatic pump and/or a hydraulic pump.

At least a portion of the cardiac assist device 100, such as the set of cups 150, may be inserted into a body of a person having problems associated with a heart of the person (e.g., the person may have a weakened heart, the heart may have problems pumping enough blood, the heart may be damaged due to one or more diseases, etc.). For example, the cardiac assist device 100 may be inserted via a sternotomy procedure, a thoracotomy procedure and/or may be inserted through an area beneath and/or between ribs of the person.

The cardiac assist device 100 may emulate natural movement of muscles of the heart, such as rotational movement (e.g., a twisting motion, a wringing motion, a spiral motion) of the heart (e.g., motion of the heart may twist in an anti-clockwise direction and/or in a clockwise direction during systole and/or during diastole). For example, the set of cups 150 may be controlled to support rotation (e.g., twisting motion) of the heart and/or increase pumping power of the heart using the pump. For example, an inner surface of the set of cups 150 may be uniform and/or pressure may be applied unevenly to the heart using the set of cups. This may prevent damage to coronary arteries of the heart. Alternatively and/or additionally, the set of cups 150 may exert pressure on left ventricles and right ventricles, providing support for both the left ventricles and the right ventricles (simultaneously). This may prevent right ventricular failure.

In some examples, the pump may conduct the fluid to the set of cups 150 using the first part of the cannula 810 and/or the second part of the cannula 502. In order to prevent infection from outside of the body (via an area that the first part of the cannula 810 and/or the second part of the cannula 502 may enter the body), one or more cuffs may be inserted in a path of two layers of muscles and/or subcutaneous tissue such that exchange of air and/or fluid between the outside of the body and/or inside of the body is prevented. The one or more cuffs may be stained with antibiotics and/or may regularly (e.g., periodically) release antibiotics in order to prevent the infection.

Figure 2:
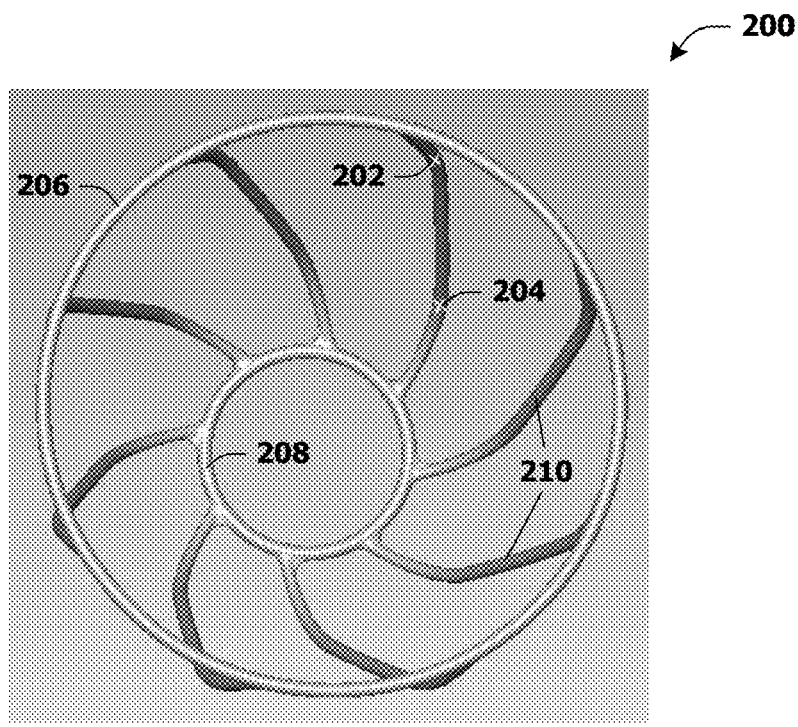
FIG. 2 is a drawing illustrating a structure of an exemplary cardiac assist device.

FIG. 2 illustrates a structure 200. For example, the structure 200 may be comprised within the cardiac assist device 100. For example, the structure 200 may be comprised within a first embodiment of the set of cups 150, such as a first set of cups 400 (e.g., illustrated in FIG. 4). The structure 200 may surround at least a portion of the heart. For example, the structure 200 may comprise an upper ring 206 and/or a lower ring 208. The upper ring 206 may have a larger diameter than a diameter of the lower ring 208. Alternatively and/or additionally, the upper ring 206 may surround a first portion of the heart. Alternatively and/or additionally, the lower ring 208 may be adjacent to a bottom of the heart. For example, the lower ring 208 may be positioned beneath the heart.

Alternatively and/or additionally, the structure 200 may comprise a plurality of columns 210 (e.g., pillars, arms, etc.). The plurality of columns 210 may connect the upper ring 206 to the lower ring 208. In some examples, each column of the plurality of columns 210 may comprise a first curvature 202 at a first point of the column and/or a second curvature 204 at a second point of the column. In some examples, the structure 200 (e.g., the upper ring 206, the lower ring 208 and/or the plurality of columns 210) may be made of a plastic. Alternatively and/or additionally, the structure 200 may be made of a silicone-based material. For example, the structure 200 may have a first level of flexibility (e.g., pliability, softness, etc.). The structure 200 may bend, twist, etc. without breaking.

Figure 3:
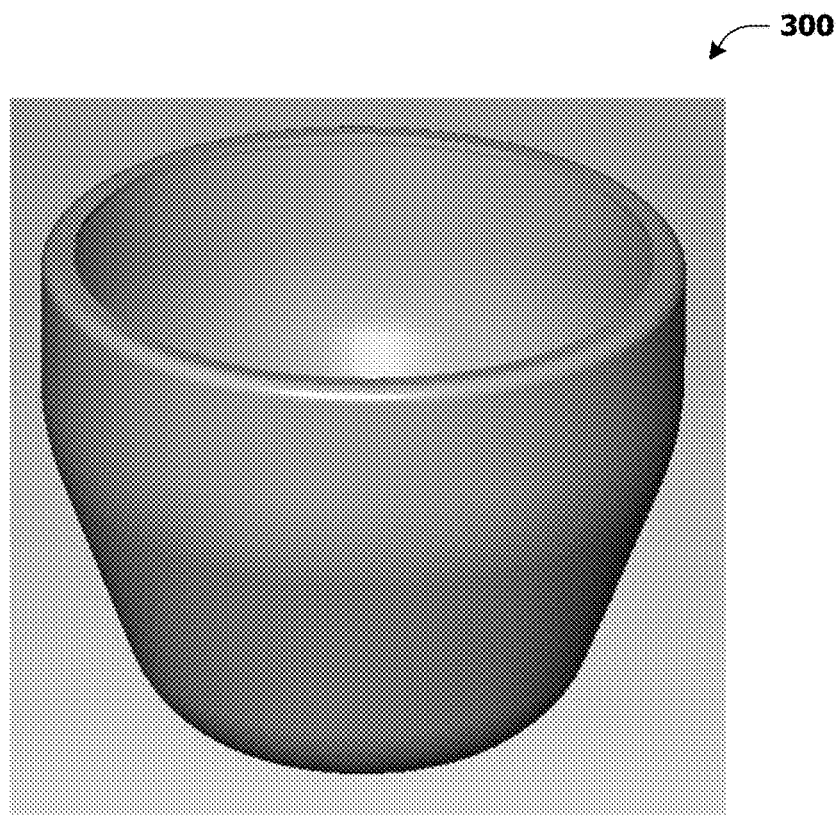
FIG. 3 is a drawing illustrating an inner cup of an exemplary cardiac assist device.

FIG. 3 illustrates an inner cup 300 of the first set of cups 400. The inner cup 300 may enclose at least a portion of the structure 200. In some examples, the inner cup 300 may comprise a plurality of layers. For example, the inner cup 300 may comprise a first layer (e.g., an inner layer) of the plurality of layers and/or a second layer (e.g., an outer layer) of the plurality of layers. The structure 200 may be positioned between the first layer and the second layer. For example, rather than the structure 200 having contact with the heart, the first layer may have contact with the heart. In some examples, the inner cup 300 may be made of a first silicone-based material. For example, the inner cup 300 may have a second level of flexibility. The inner cup 300 may bend, twist, etc. without breaking. In some examples, the first layer of the inner cup 300 may be made of a biocompatible material. Alternatively and/or additionally, the first layer may be made of the first silicone-based material.

Figure 4:
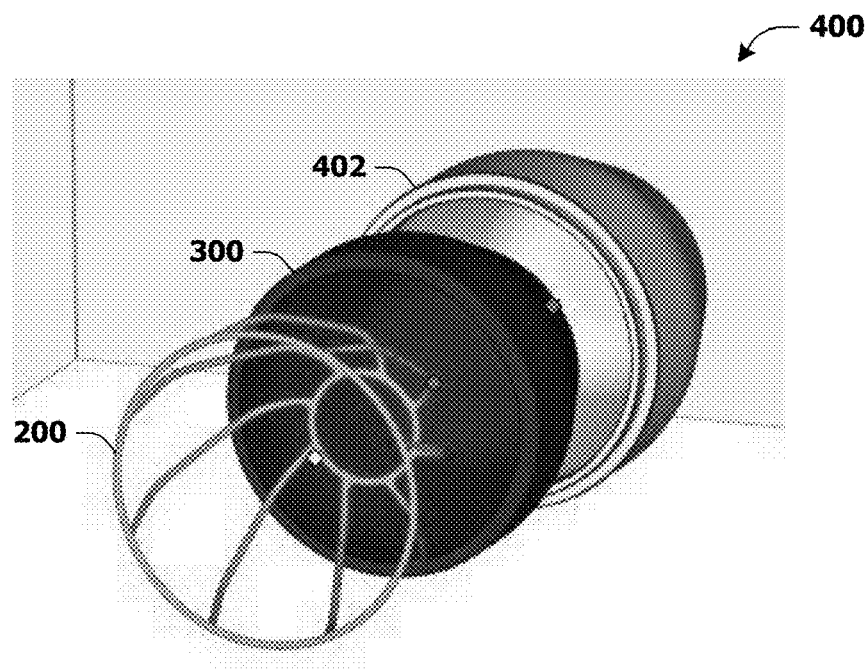
FIG. 4 is a drawing illustrating an exemplary set of cups comprising a structure, an inner cup and/or an outer cup.

FIG. 4 illustrates the first set of cups 400 comprising the structure 200, the inner cup 300 and/or an outer cup 402. In some examples, the inner cup 300 and/or the structure 200 may be positioned within the outer cup 402. For example, the outer cup 402 may enclose at least a portion of the inner cup 300. For example, the inner cup 300 may be positioned within the outer cup 402 such that a top of the outer cup 402 extends above a top of the inner cup 300. Alternatively and/or additionally, the top of the inner cup 300 may extend above the top of the outer cup 402. Alternatively and/or additionally, the top of the outer cup 402 and/or the top of the inner cup 300 may be level with each other.

In some examples, the outer cup 402 may comprise an opening (e.g., a hole) which may connect to the first part of the cannula 502. For example, the first part of the cannula 502 may be mounted on the opening. For example, the opening and/or the first part of the cannula 502 may be positioned on a side of the outer cup 402, between a bottom of the outer cup 402 and the top of the outer cup 402 (e.g., similar to a position of the first part of the cannula 502 illustrated in FIG. 5). Alternatively and/or additionally, the opening and/or the first part of the cannula 502 may be positioned on the bottom side of the outer cup 402. For example, the opening and/or the first part of the cannula 502 may be positioned adjacent to the lower ring 208 (e.g., opposite the lower ring 208, beneath the lower ring 208).

In some examples, one or more surfaces of the first set of cups 400 (e.g., first surfaces of the inner cup 300 and/or second surfaces of the outer cup 402) may be polished and/or smooth. Alternatively and/or additionally, one or more second surfaces of the first set of cups 400 may be covered with a layer (e.g., coating) of hydrogel and/or may have minimal post-operative adhesion. The one or more surfaces of the first set of cups 400 being polished and/or smooth and/or the one or more second surfaces of the first set of cups 400 being covered with hydrogel may result in minimized erosion between the first set of cups 400 and the heart (and/or other parts of the body).

In some examples, the outer cup 402 may be made of a second silicone-based material. For example, the outer cup 402 may have a second level of flexibility. For example, the second silicone-based material of the outer cup 402 may be different than the first silicone-based material of the inner cup 300. For example, the first silicone-based material of the inner cup 300 may be a first type of silicone having a first density. Alternatively and/or additionally, the second silicone-based material of the outer cup 402 may be a second type of silicone having a second density. In some examples, the second density may be higher than the first density. For example, the second density may be five times higher than the first density, 10 times higher than the first density, 15 times higher than the first density, etc. For example, due to the inner cup 300 having the first type of silicone and the outer cup 402 having the second type of silicone, the outer cup 402 may not bend and/or twist under conditions that may cause the inner cup 300 and/or the structure 200 to bend and/or twist.

In some examples, the first level of flexibility of the structure 200, the second level of flexibility of the inner cup 300 and/or the third level of flexibility of the outer cup 402 may allow the first set of cups 400 to be inserted into the body and/or positioned surrounding the heart from between the ribs, under the ribs and/or using a relatively small incision of the body. For example, it may not be necessary to perform a large incision, because the first set of cups 400 may be folded and/or made smaller (relative to a volume of the first set of cups 400) when being placed inside of the body (due to the first level of flexibility of the structure 200, the second level of flexibility of the inner cup 300 and/or the third level of flexibility of the outer cup 402).

In some examples, gas (and/or liquid) (e.g., oxygen, air and/or a different gas) may be conducted into a space between the outer cup 402 and the inner cup 300 using the pump. For example, the gas may be conducted through the second part of the cannula 810, the first part of the cannula 502 and/or through the opening into the space. In some examples, the top of the outer cup 402 (and/or a different part of the outer cup 402) may be connected to the top of the inner cup 300 (and/or a different part of the inner cup 300) such that the gas does not exit the space (e.g., the space may be sealed).

In some examples, the gas being conducted into the space may cause a first motion of the structure 200 and/or the inner cup 300. For example, the first motion of the structure 200 and/or the inner cup 300 may be associated with a first rotation of the lower ring 208 in a first direction. Alternatively and/or additionally, the first motion may be a first twisting motion (e.g., a spiral motion) of the structure 200 and/or the inner cup 300 in the first direction. For example, the first direction may be a clockwise direction (and/or an anti-clockwise direction).

In some examples, the gas being conducted into the space may cause the inner cup 300 and/or the structure 200 to cling (e.g., become attached) to the heart. For example, at least a portion of the inner cup 300 (e.g., a lower portion of the inner cup 300) and/or at least a portion of the structure 200 (e.g., a lower portion of the structure 200 that does not include the upper ring 206) may move upwards (e.g., in a spiral and/or twisting motion) towards the heart and/or become attached to the heart. For example, during the first motion of the structure 200 and/or the inner cup 300, the structure 200 and/or the inner cup 300 may move (e.g., twist and/or rotate) in a manner supporting rotation (e.g., and/or twisting motion) of the heart in the first direction. For example, the gas being conducted into the space may cause the plurality of columns 210 of the structure 200 to bend and/or move such that the structure 200 and/or the inner cup 300 twist (move in the spiral motion) in accordance with rotation of the heart (e.g., while the lower ring 208 rotates in the first direction). Further, the plurality of columns 210 of the structure 200 may bend and/or move such that the structure 200 and/or the inner cup 300 cling to the heart (e.g., move upwards towards the heart and/or become attached to the heart). Alternatively and/or additionally, the first motion of the structure 200 and/or the inner cup 300 may not cause friction and/or erosion (and/or may cause minimal friction and/or erosion) between the inner cup 300 and the heart. Alternatively and/or additionally, the first motion of the structure 200 and/or the inner cup 300 may not cause damage to heart tissue. In some examples, the first motion of the structure 200 and/or the inner cup 300 may increase the pumping power of the heart and/or may support rotation (e.g., and/or twisting motion) of the heart in the first direction. In some examples, the first rotation may be a rotation of between 15 to 20 degrees (and/or a different value) in the first direction. Alternatively and/or additionally, the rotation (e.g., and/or twisting motion) of the heart in the first direction may be between 15 to 20 degrees (and/or a different value).

Alternatively and/or additionally, the gas may be conducted from the space to outside of the outer cup 402 using the pump. For example, the gas may be conducted through the opening, the first part of the cannula 502 and/or the second part of the cannula 810 to outside of the body using the pump. In some examples, the gas being conducted from the space to outside of the space may cause a second motion of the structure 200 and/or the inner cup 300. For example, the second motion of the structure 200 and/or the inner cup 300 may be associated with a second rotation of the lower ring 208 in a second direction. Alternatively and/or additionally, the second motion may be a second twisting motion (e.g., a spiral motion) of the structure 200 and/or the inner cup 300 in the second direction. The second direction may be different and/or opposite to the first direction. For example, the first direction may be an anti-clockwise direction (and/or a clockwise direction if the first direction is an anti-clockwise direction).

In some examples, during the second motion of the structure 200 and/or the inner cup 300, the structure 200 and/or the inner cup 300 may move (e.g., twist and/or rotate) in a manner supporting rotation (e.g., and/or twisting motion) of the heart in the second direction. Alternatively and/or additionally, the second motion of the structure 200 and/or the inner cup 300 may not cause friction and/or erosion (and/or may cause minimal friction and/or erosion) between the inner cup 300 and the heart. Alternatively and/or additionally, the second motion of the structure 200 and/or the inner cup 300 may not cause damage to the heart tissue. In some examples, the second motion of the structure 200 and/or the inner cup 300 may increase the pumping power of the heart and/or may support rotation (e.g., and/or twisting motion) of the heart in the second direction. In some examples, the second rotation may be a rotation of between 15 to 20 degrees (and/or a different value) in the second direction. Alternatively and/or additionally, the rotation of the heart in the second direction may be between 15 to 20 degrees (and/or a different value). In some examples, responsive to the second rotation, the structure 200, the inner cup 300 and/or the heart may be in a state similar to a state of the structure 200, the inner cup 300 and/or the heart before the first motion occurs.

In some examples, a combination of the gas being conducted into the space and the gas being conducted from the space to outside of the space may consist of a pump cycle corresponding to a heart rotation cycle. For example, the heart rotation cycle may comprise a period that the heart rotates in the first direction and the heart rotates in the second direction. For example, the pump cycle may be synchronized with the heart rotation cycle such that rotation of the heart in the first direction and rotation (e.g., and/or twisting motion) of the heart in the second direction is supported by the cardiac assist device 100. For example, while the heart rotates (e.g., and/or twists) in the first direction, the first motion in the first direction of the structure 200 and/or the inner cup 300 occurs to support and/or assist the heart in rotating (e.g., and/or twisting) in the first direction. While the heart rotates (e.g., and/or twists) in the second direction, the second motion in the second direction of the structure 200 and/or the inner cup 300 occurs to support and/or assist the heart in rotating (e.g., and/or twisting) in the second direction. For example, the pump cycle may be performed periodically, at a rate. The rate of the pump cycle may be synchronized with the heart. For example, the rate of the pump cycle may be based upon a heart rate of the heart. In some example, the rate of the pump cycle may be around 80 pump cycles per minute (e.g., between 70 and 90 pump cycles per minute). Alternatively and/or additionally, the rate of the pump cycle may be greater than 80 pump cycles per minute. Alternatively and/or additionally, the rate of the pump cycle may be less than 80 pump cycles per minute.

For example, the cardiac assist device 100 may comprise one or more sensors configured to detect one or more measurements associated with the heart. For example, the one or more sensors may comprise the one or more electrocardiogram leads 804. The one or more electrocardiogram leads 804 may comprise two (or more) electrocardiogram leads. In some examples, the one or more sensors may be connected to the controller 808. The controller 808 may control the pump based upon the one or more measurements. The one or more measurements may comprise a heart rate measurement of the heart. Accordingly, the controller 808 may control the pump such that the rate of the pump cycle is controlled based upon the heart rate measurement and/or such that the rate of the pump cycle is synchronized with the heart rate of the heart.

In some examples, rather than controlling the first set of cups 400 using the pump, the first set of cups 400 may be controlled using a motor. For example, the motor may be configured to rotate the lower ring 208 in the first direction and/or in the second direction. In some examples, rotating the lower ring 208 in the first direction may cause the first motion of the inner cup 300 and/or the structure 200 (for supporting rotation and/or twisting motion of the heart in the first direction). Alternatively and/or additionally, rotating the lower ring 208 in the second direction may cause the second motion of the inner cup 300 and/or the structure 200 (for supporting rotation and/or twisting motion of the heart in the second direction).

In some examples, the motor may be connected to the outer cup 402. Alternatively and/or additionally, the first set of cups 400 may not comprise the outer cup 402 in an embodiment of the first set of cups 400 being controlled by the motor. For example, the motor may be connected to the inner cup 300. For example, the motor may be connected to a plate. The plate may be connected to the inner cup 300. The motor may rotate the inner cup 300 and/or the lower ring 208 by rotating the plate. In some examples, the motor may be positioned adjacent to the first set of cups 400 (e.g., beneath the first set of cups 400). In some examples, in embodiments where the motor is used to control the first set of cups 400 rather than the pump, an echocardiogram may be more easily performed (than in embodiments where the pump is used to control the first set of cups 400). Alternatively and/or additionally, in embodiments where the motor is used to control the first set of cups 400 rather than the pump, the first set of cups 400 may be designed such that more of the heart is enclosed by the first set of cups 400 (than in embodiments where the pump is used to control the first set of cups 400).

In some examples, one or more sizes of the first set of cups 400 (e.g., a size of the structure 200, a size of the inner cup 300 and/or a size of the outer cup 402) may be configured based upon the heart. For example, a size of the heart may be determined (e.g., by scanning the heart using one or more techniques). The first set of cups 400 may be designed and/or produced based upon the size of the heart. Alternatively and/or additionally, the first set of cups 400 may be selected, based upon the size of the heart, from a plurality of sets of cups having different sizes associated with different heart sizes. In some examples, the first set of cups 400 may be sutured to the heart. For example, the outer cup 402, the inner cup 300 and/or the structure 200 (e.g., the upper ring 206) may be sutured to a pericardium of the heart. Alternatively and/or additionally, the outer cup 402, the inner cup 300 and/or the structure 200 (e.g., the upper ring 206) may be fastened to the pericardium of the heart using one or more techniques other than suturing.

Figure 5:
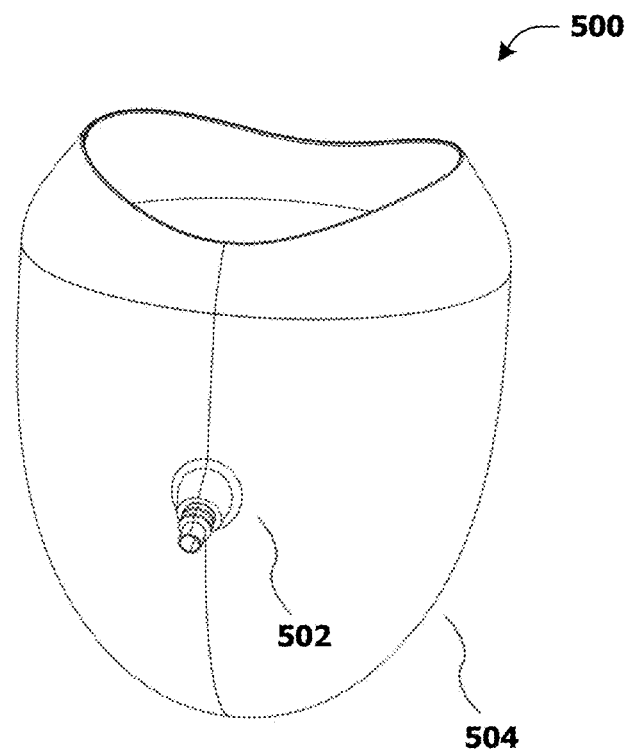
FIG. 5 is a drawing illustrating a second set of cups of an exemplary cardiac assist device.

FIG. 5 illustrates a second set of cups. For example, the second set of cups may be a second embodiment of the set of cups 150 (which may be used in place of the first set of cups 400). For example, the second set of cups may comprise a (single) cup 500. In some examples, the cup 500 may comprise an outer layer 504. The outer layer 504 may be made of a third silicone-based material. For example, the outer layer 504 may have a fourth level of flexibility.

In some examples, the outer layer 504 may comprise a second opening (e.g., a hole) which may connect to the first part of the cannula 502. For example, the first part of the cannula 502 may be mounted on the second opening. For example, the second opening and/or the first part of the cannula 502 may be positioned on a side of the outer layer 504. Alternatively and/or additionally, the second opening and/or the first part of the cannula 502 may be positioned on a bottom side of the outer layer 504.

Figure 6:
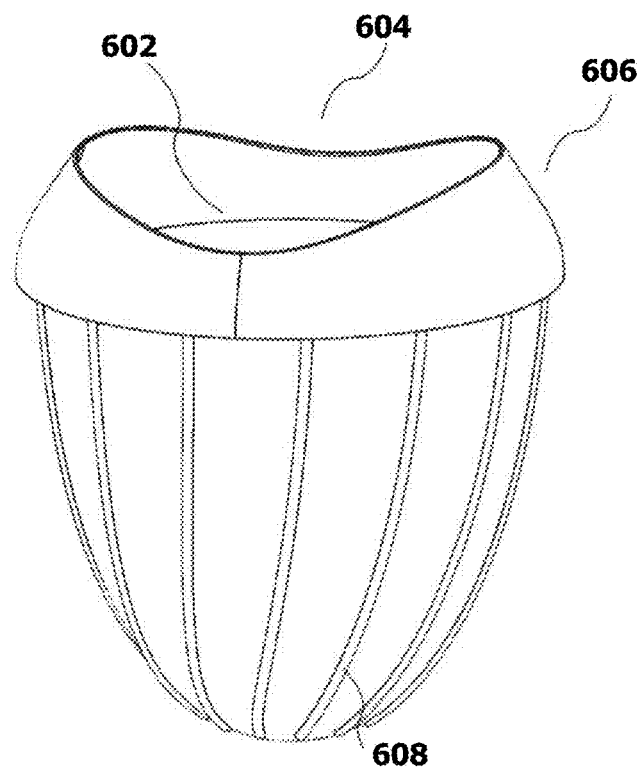
FIG. 6 is a drawing illustrating an exemplary inner layer of a cup.

FIG. 6 illustrates an inner layer 604 of the cup 500. The inner layer 604 of the cup 500 may be made of a fourth silicone-based material. For example, the inner layer 604 may have a fifth level of flexibility. In some examples, the fifth level of flexibility may enable the heart to be inserted into the inner layer 604. In some examples, the cup 500 may comprise an upper portion 606 of the cup 500. For example, the upper portion 606 of the cup 500 may be fixed (e.g., secured) to a portion of the heart such that the cup 500 is secured to the heart. In some examples, the upper portion 606 of the cup 500 may be fixed around a portion of the heart associated with an intersection of ventricles and atrials of the heart. In some examples, the inner layer 604 may enclose at least a portion of the atrials of the heart.

Figure 7:
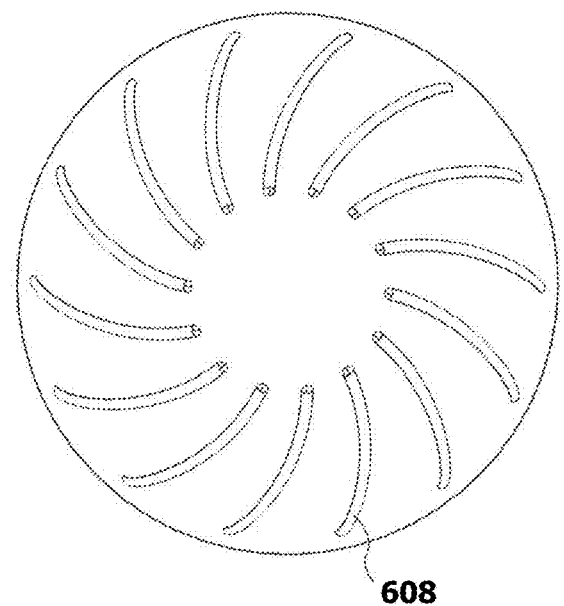
FIG. 7 is a drawing illustrating an overhead view of an exemplary inner layer of a cup.

In some examples, an inner surface 602 of the inner layer 604 may comprise a second plurality of columns 608 (e.g., pillars, arms, etc.). An overhead view of the second plurality of columns 608 is illustrated in FIG. 7. The second plurality of columns 608 may be made of a fifth silicone-based material. The second plurality of columns 608 may be coupled to the inner surface 602 of the inner layer 604. In some examples, each column of the second plurality of columns 608 may be curved. Alternatively and/or additionally, columns of the second plurality of columns 608 may not intersect with each other. In some examples, a number of columns of the second plurality of columns 608 may be between 15 and 25 (and/or a different number of columns).

In some examples, the fourth silicone-based material of the inner layer 604 may be different than the fifth silicone-based material of the second plurality of columns 608. For example, the fourth silicone-based material of the inner layer 604 may be a third type of silicone having a third density. Alternatively and/or additionally, the fifth silicone-based material of the second plurality of columns 608 may be a fourth type of silicone having a fourth density. In some examples, the fourth density may be higher than the third density. For example, the fourth density may be five times higher than the third density, 10 times higher than the third density, 15 times higher than the third density, etc.

In some examples, the inner surface 602 of the inner layer 604 may be polished and/or smooth. Alternatively and/or additionally, the inner surface 602 of the inner layer 604 may be covered with a layer (e.g., coating) of hydrogel and/or may have minimal post-operative adhesion. The inner surface 602 of the inner layer 604 being polished and/or smooth and/or the inner surface 602 of the inner layer 604 being covered with hydrogel may result in minimized erosion between the inner surface 602 of the inner layer 604 and/or the heart.

In some examples, the gas may be conducted into a second space between the outer layer 504 of the cup 500 and the inner layer 604 of the cup 500. For example, the gas may be conducted through the second part of the cannula 810, through the first part of the cannula 502 and/or through the second opening into the second space. In some examples, the inner layer 604 and/or the outer layer 504 may be connected to the upper portion 606 of the cup 500 such that the gas does not exit the second space (e.g., the second space may be sealed).

In some examples, the gas being conducted into the second space may cause a third motion of the inner layer 604 and/or the second plurality of columns 608. For example, the third motion of the inner layer 604 and/or the second plurality of columns 608 may be a third twisting motion (e.g., a spiral motion) of the inner layer 604 and/or the second plurality of columns 608 in the first direction.

The gas being conducted into the second space may cause the inner layer 604 and/or the second plurality of columns 608 to cling (e.g., become attached) to the heart. For example, during the third motion of the inner layer 604 and/or the second plurality of columns 608, the inner layer 604 and/or the second plurality of columns 608 may move (e.g., twist and/or rotate) in a manner supporting rotation (e.g., and/or twisting motion) of the heart in the first direction. For example, the gas being conducted into the second space may cause the second plurality of columns 608 to bend and/or move such that the inner layer 604 and/or the second plurality of columns 608 twist (move in the spiral motion) in accordance with rotation of the heart. Further, the second plurality of columns 608 may bend and/or move such that the inner layer 604 and/or the second plurality of columns 608 cling to the heart (e.g., move upwards towards the heart and/or become attached to the heart). Alternatively and/or additionally, the third motion of the inner layer 604 and/or the second plurality of columns 608 may not cause friction and/or erosion (and/or may cause minimal friction and/or erosion) between the inner layer 604 and/or the second plurality of columns 608 and the heart. Alternatively and/or additionally, the third motion of the inner layer 604 and/or the second plurality of columns 608 may not cause damage to heart tissue. In some examples, the third motion of the inner layer 604 and/or the second plurality of columns 608 may increase the pumping power of the heart and/or support rotation (e.g., and/or twisting motion) of the heart in the first direction.

Alternatively and/or additionally, the gas may be conducted from the second space to outside of the outer layer 504 using the pump. For example, the gas may be conducted through the second opening, the first part of the cannula 502 and/or the second part of the cannula 810 to outside of the body using the pump. In some examples, the gas being conducted from the second space to outside of the second space may cause a fourth motion of the inner layer 604 and/or the second plurality of columns 608. For example, the fourth motion of the inner layer 604 and/or the second plurality of columns 608 may be a fourth twisting motion (e.g., a spiral motion) of the inner layer 604 and/or the second plurality of columns 608 in the second direction.

In some examples, during the fourth motion of the inner layer 604 and/or the second plurality of columns 608, the inner layer 604 and/or the second plurality of columns 608 may move (e.g., twist and/or rotate) in a manner supporting rotation (e.g., and/or twisting motion) of the heart in the second direction. Alternatively and/or additionally, the fourth motion of the inner layer 604 and/or the second plurality of columns 608 may not cause friction and/or erosion (and/or may cause minimal friction and/or erosion) between the inner layer 604 and the heart. Alternatively and/or additionally, the fourth motion of the inner layer 604 and/or the second plurality of columns 608 may not cause damage to the heart tissue. In some examples, the fourth motion of the inner layer 604 and/or the second plurality of columns 608 may increase the pumping power of the heart and/or support rotation (e.g., and/or twisting motion) of the heart in the second direction.

It may be appreciated that rather than controlling the cup 500 using the pump, the cup 500 may be controlled using the motor.

Figure 8:
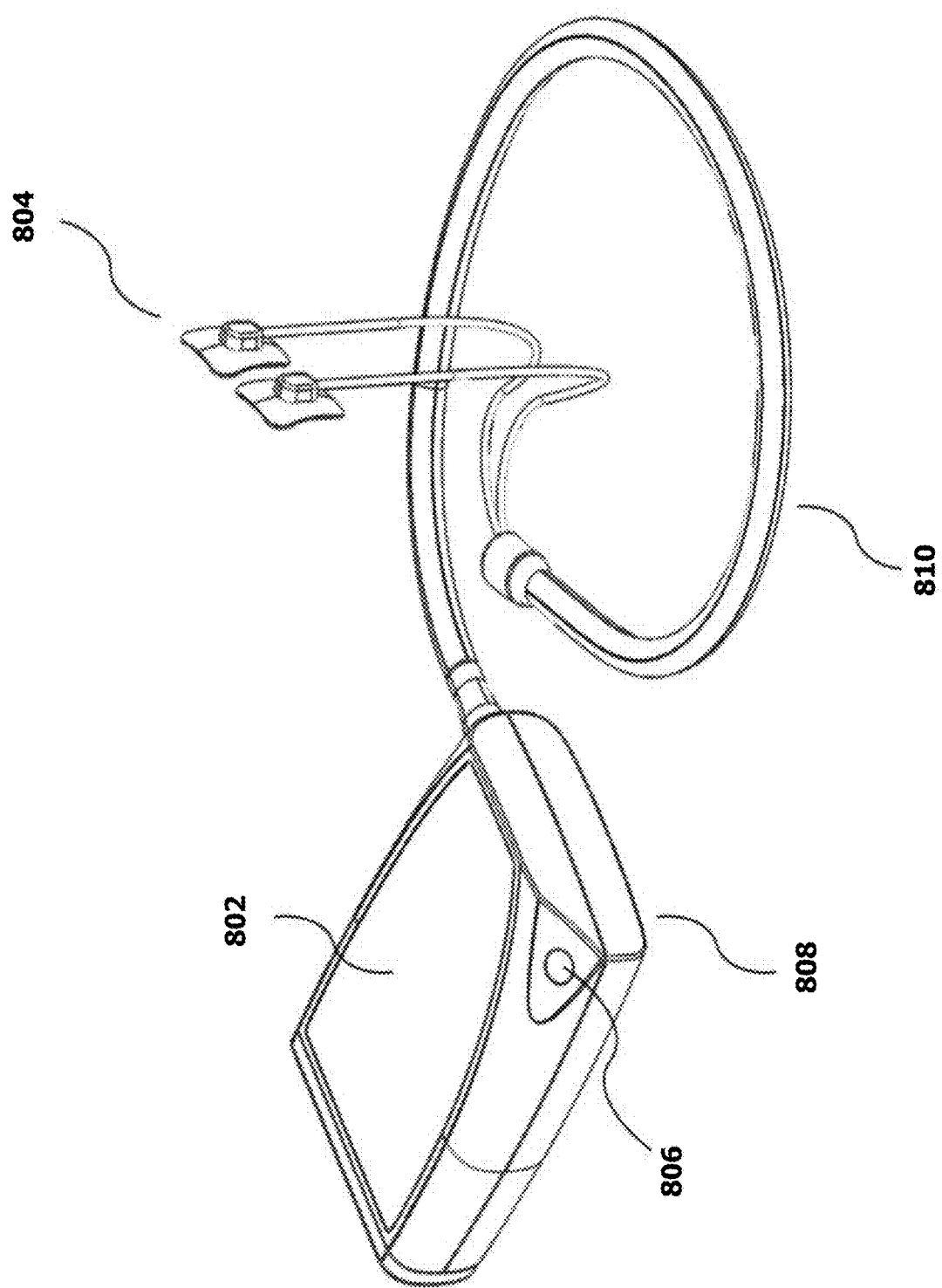
FIG. 8 is a drawing illustrating a controller, a second part of a cannula and/or one or more electrocardiogram leads of an exemplary cardiac assist device.

FIG. 8 illustrates the controller 808, the second part of the cannula 810 and/or the one or more electrocardiogram leads 804. For example, a lumen diameter of the second part of the cannula 810 may be between 16 and 20 French (and/or a different value). The second part of the cannula 810 may be connected to the pump of the controller 808. In some examples, the second part of the cannula 810 may be connected to first part of the cannula 502 by inserting the second part of the cannula 810 into the body from beneath the ribs (and/or from a different location). Alternatively and/or additionally, the one or more electrocardiogram leads 804 may be positioned on a chest of the body (and/or a different location of the body).

In some examples, the controller 808 may comprise a screen 802. For example, the screen 802 may be a touchscreen that may be used to control settings associated with the controller 808. Alternatively and/or additionally, the one or more measurements, such as the heart rate measurement, and/or output settings associated with the controller 808 may be displayed via the screen 802. In some examples, the controller 808 may comprise a power button 806 (e.g., an on-off switch corresponding to the screen 802). In some examples, the controller 808 may comprise a single battery. Alternatively and/or additionally, the controller 808 may comprise a plurality of batteries (e.g., two batteries, three batteries, etc.), such that when energy of one battery of the plurality of batteries is depleted, a different battery of the plurality of batteries may automatically be used. In some examples, a battery may last for around 6 hours (and/or a different amount of time) before it is depleted.

In some examples, rather than using batteries, a power generating device may be used to generate power using motion associated with the body. For example, the power generating device may be connected to the controller 808, the pump and/or the motor. In some examples, the power generating device may be inserted inside the body. For example, the power generating device may use motion of respiration of lungs of the body in order to generate the power to power the controller 808, the pump and/or the motor. Alternatively and/or additionally, the power generating device may not be inserted inside the body. For example, the power generating device may use motion of legs of the body, arms of the body, etc. in order to generate the power to power the controller 808, the pump and/or the motor.

Figure 9:
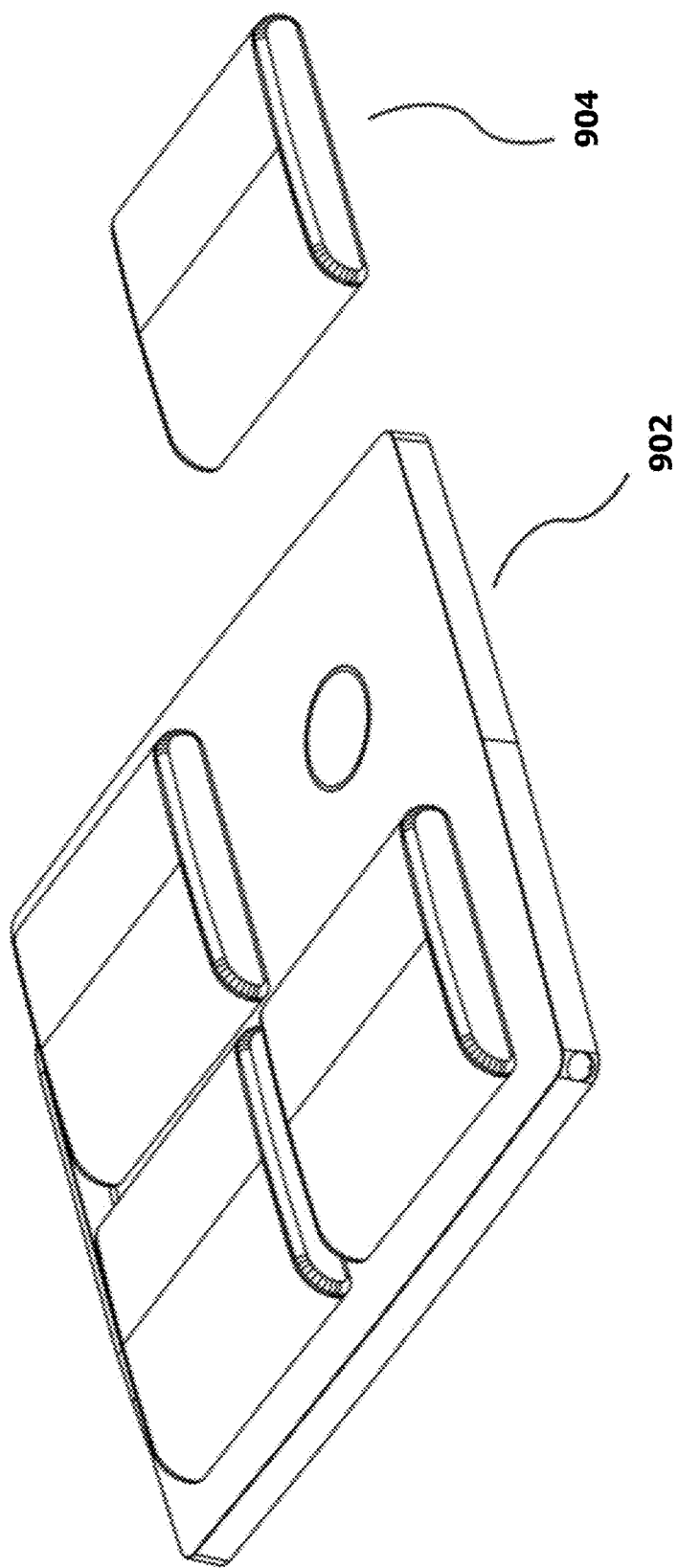
FIG. 9 is a drawing illustrating a wireless charger of an exemplary cardiac assist device.

FIG. 9 illustrates the first battery charger 902. For example, the first battery charger 902 may be used for the cardiac assist device 100. In some examples, the first battery charger 902 may charge a second plurality of batteries, such as a second battery 904, wirelessly (e.g., using wireless charging technology). Alternatively and/or additionally, the first batter charger 902 may be a wireless charger and/or may comprise one or more built in batteries such that the first battery charger 902 may charge the second plurality of batteries without needing access to an external power source (e.g., an outlet). In some examples, each battery of the second plurality of batteries may be a lithium ion battery (and/or a different type of battery).

Figure 10:
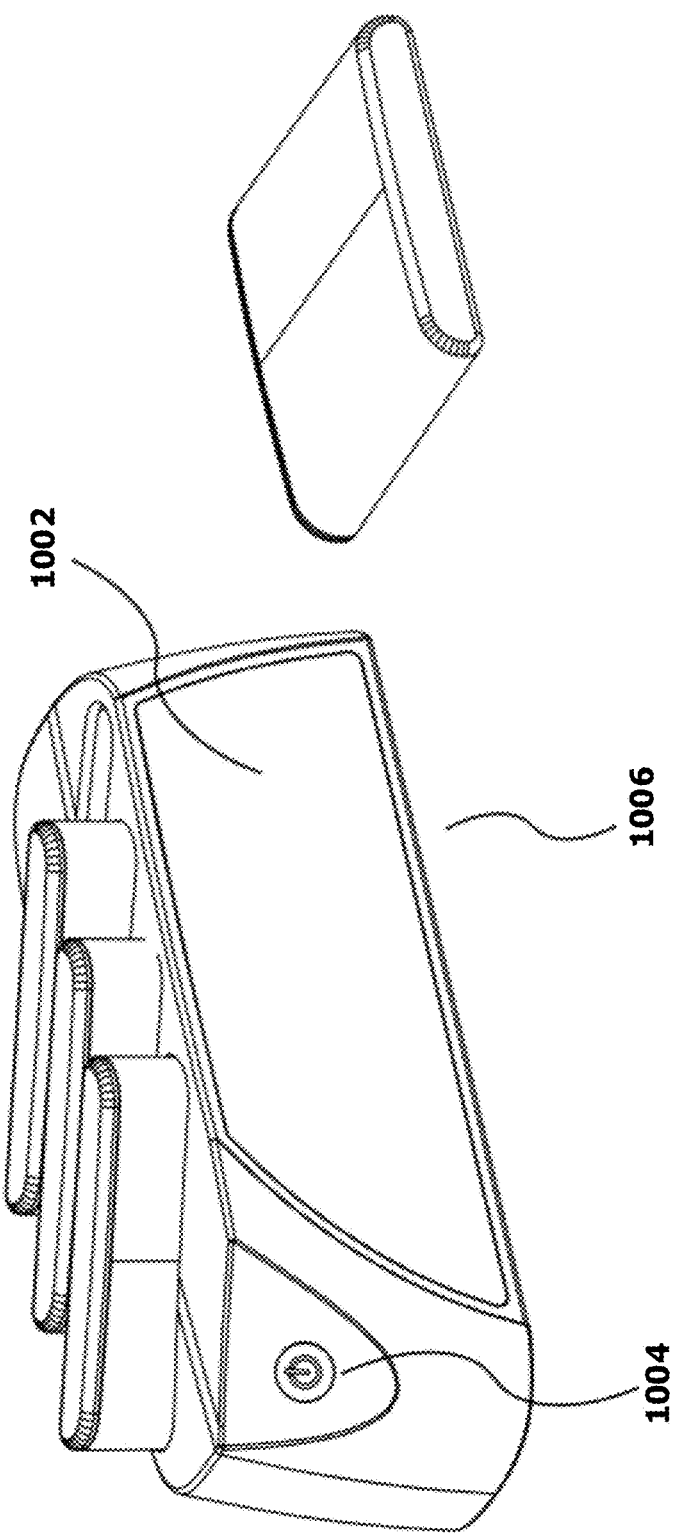
FIG. 10 is a drawing illustrating a second battery charger of an exemplary cardiac assist device.

FIG. 10 illustrates the second battery charger 1006. For example, the second battery charger 1006 may be used for the cardiac assist device 100 (in addition to the first battery charger 902). In some examples, the second battery charger 1006 may comprise a second screen 1002. For example, the second screen 1002 may display the one or more measurements, such as the heart rate measurement, and/or output settings associated with the controller 808. Alternatively and/or additionally, the second screen 1002 may display charging states associated with batteries being charged using the second battery charger 1006. In some examples, the second battery charger 1006 may be a wired battery charger connected to an alternating current (AC) network (via an outlet). The second battery charger 1006 may comprise a second power button 1004 (e.g., an on-off switch corresponding to the second screen 1002, an on-off switch corresponding to charging batteries, etc.).

Figure 11:
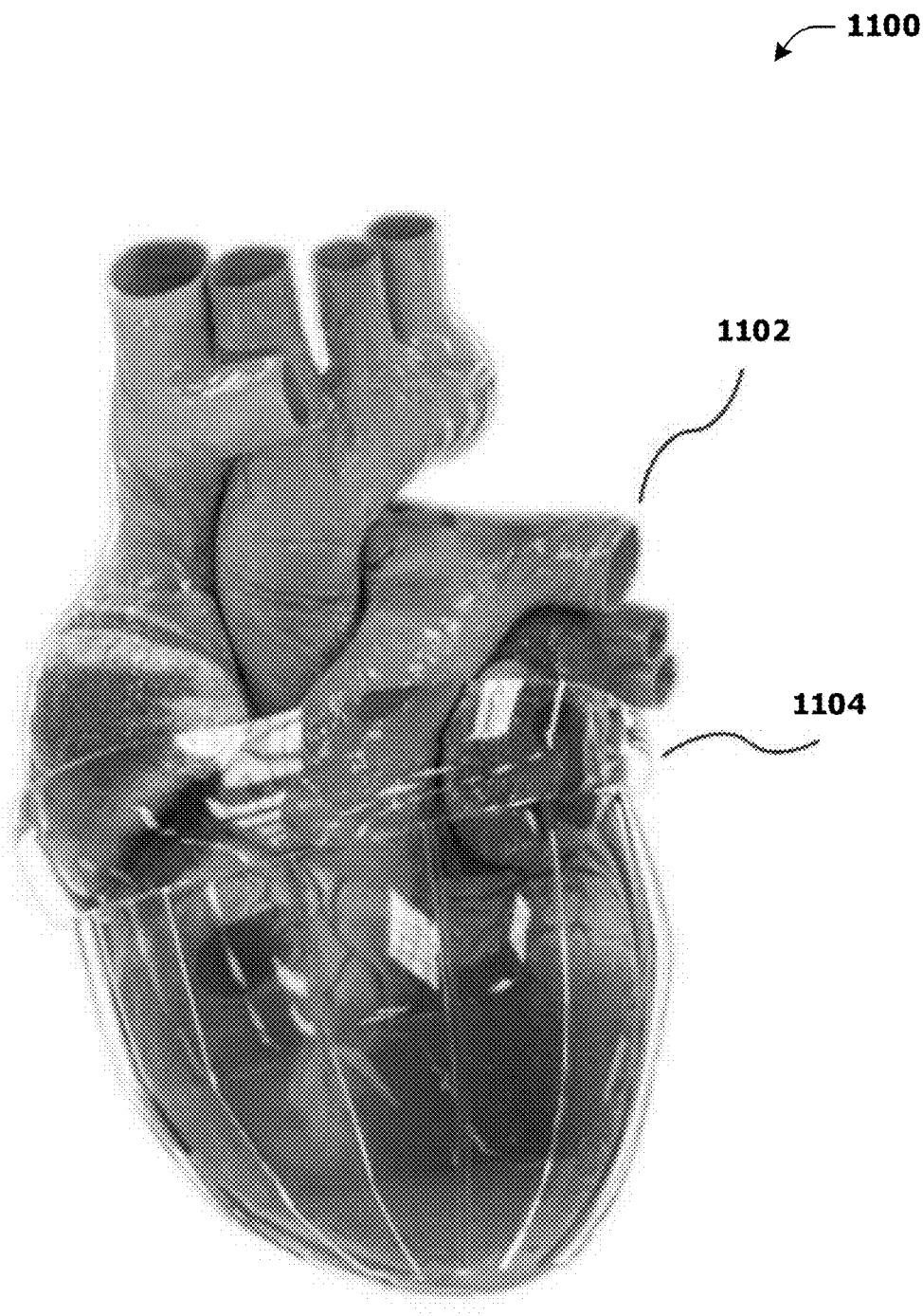
FIG. 11 is a drawing illustrating an inner layer of a cup enclosing a portion of a heart.

FIG. 11 illustrates a view 1100 of the inner layer 604 of the cup 500 enclosing a portion of a heart 1102. For example, the heart 1102 may be inserted (e.g., embedded) inside the inner layer 604 of the cup 500. The inner layer 604 of the cup 500 may (completely) enclose ventricles of the heart 1102. The upper portion 606 may be positioned adjacent to atrials 1104 of the heart 1102 such that the inner layer 604 of the cup 500 is fixed to the heart 1102 and/or such that the inner layer 604 of the cup 500 does not separate from the heart 1102.

Figure 12:
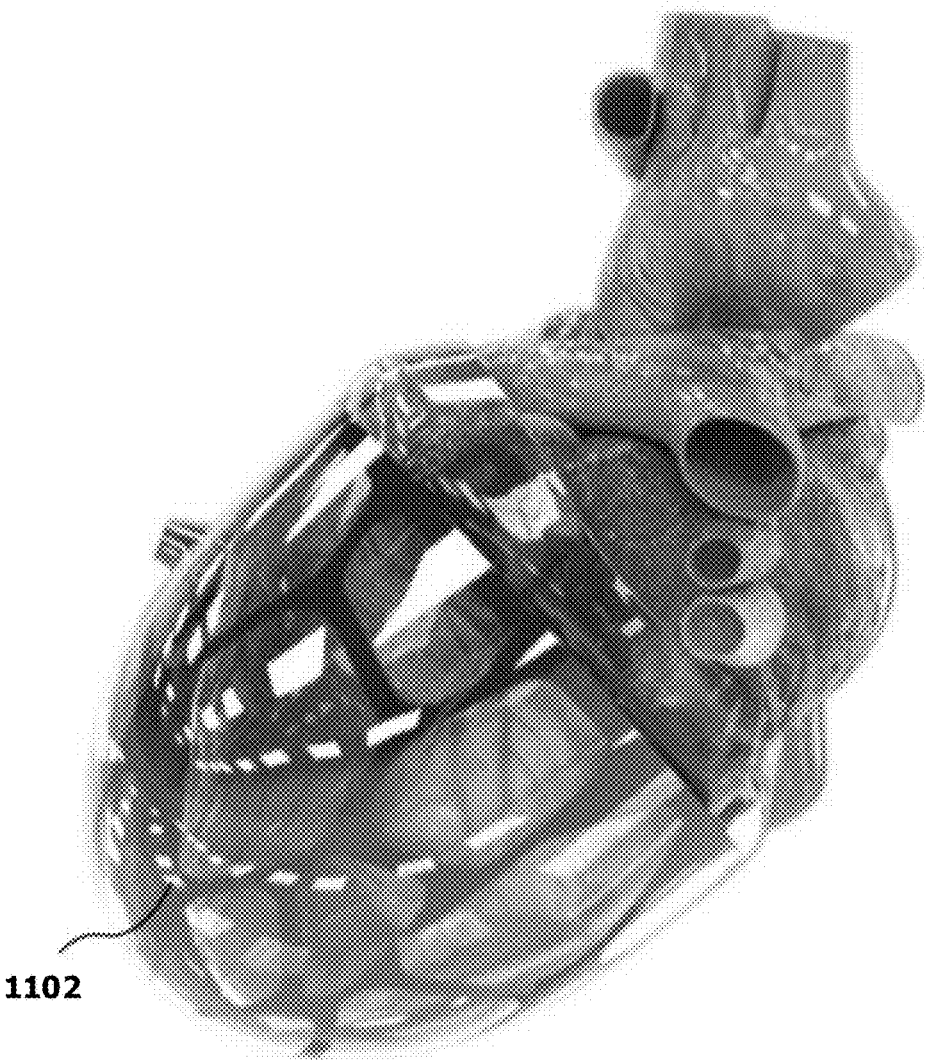
FIG. 12 is a drawing illustrating a cup enclosing a portion of a heart.

FIG. 12 illustrates a view 1200 of the cup 500 enclosing the portion of the heart 1102. For example, in the view 1200, the gas may not be in the second space between the inner layer 604 of the cup 500 and the outer layer 504 of the cup 500. In some examples, responsive to the gas being conducted into the second space, the second space may become larger and/or the inner layer 604 may become attached to the heart 1102. Further, responsive to the gas being conducted into the second space, the third motion (e.g., the third twisting motion) of the inner layer 604 and/or the second plurality of columns 608 may occur.

Figure 13:
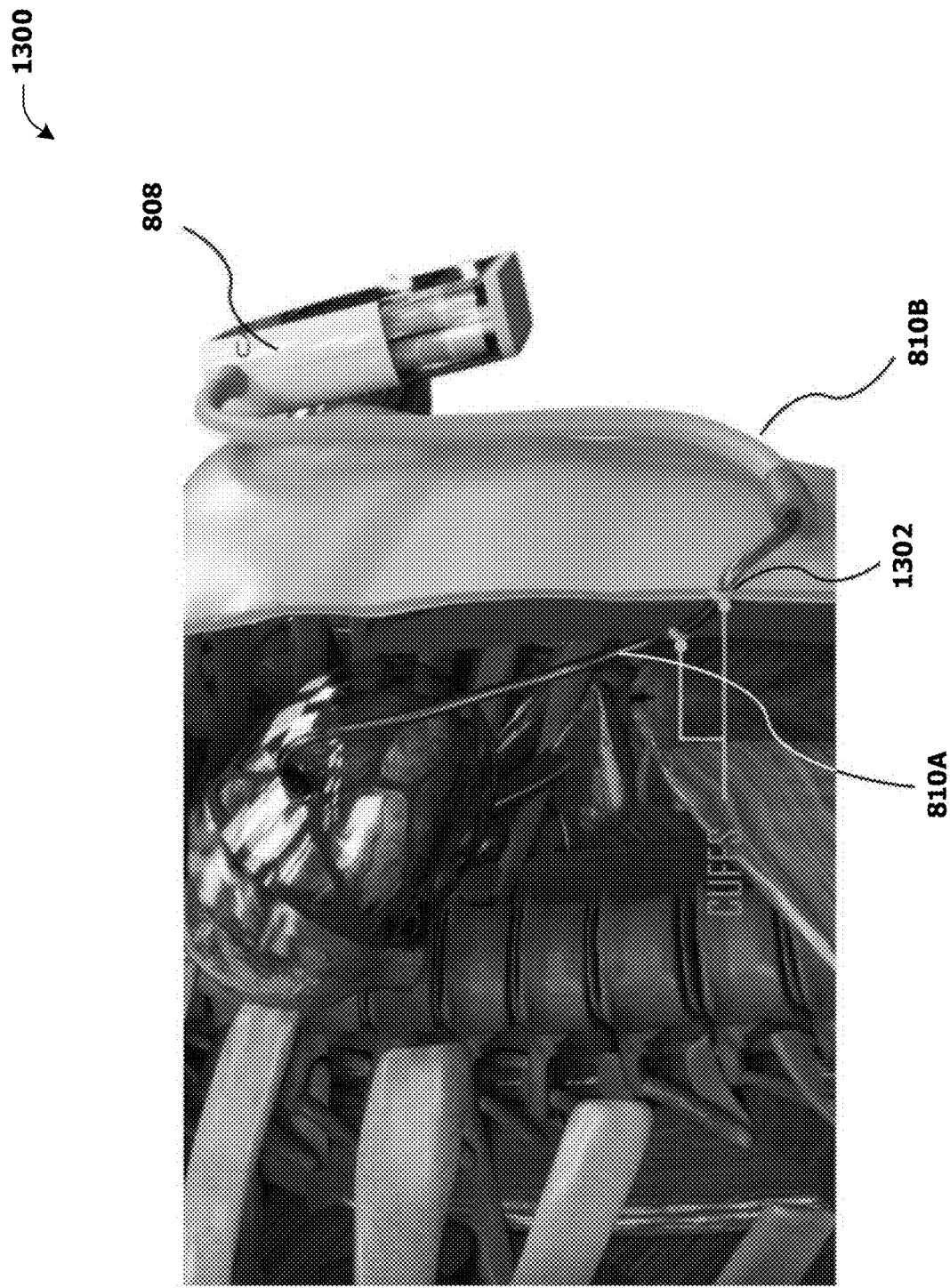
FIG. 13 is a drawing illustrating a second part of a cannula connected to a controller and/or to a set of cups.

FIG. 13 illustrates a view 1300 of the second part of the cannula 810 connected to the controller 808 and/or to the set of cups 150 (e.g., the first set of cups 400 and/or the cup 500). For example, the second part of the cannula 810 may comprise a first section 810A of the second part of the cannula 810 and/or a second section 8106 of the second part of the cannula 810. For example, at least a portion of the first section 810A of the second part of the cannula 810 may be inserted into the body. In some examples, the first section 810A of the second part of the cannula 810 may be inserted into the body through an anterior part of the body and/or below the ribs of the body.

Alternatively and/or additionally, the second section 8106 of the second part of the cannula 810 may be outside of the body. In some examples, a diameter of the second section 8106 of the second part of the cannula 810 may be greater than a diameter of the first section 810A of the second part of the cannula 810. Alternatively and/or additionally, one or more cuffs 1302 may be used in the second part of the cannula 810. For example, a first cuff of the one or more cuffs 1302 may be in muscles of the body and/or a second cuff of the one or more cuffs 1302 may be in a subcutaneous layer of the body. The one or more cuffs 1302 may prevent the exchange of air and/or fluid between the outside of the body and/or the inside of the body. Alternatively and/or additionally, the one or more cuffs 1302 may comprise fibroblast growth factor and/or antibiotics. The one or more cuffs 1302 may regularly (e.g., periodically, gradually) release the fibroblast growth factor and/or the antibiotics in order to prevent infection.

Figure 14:
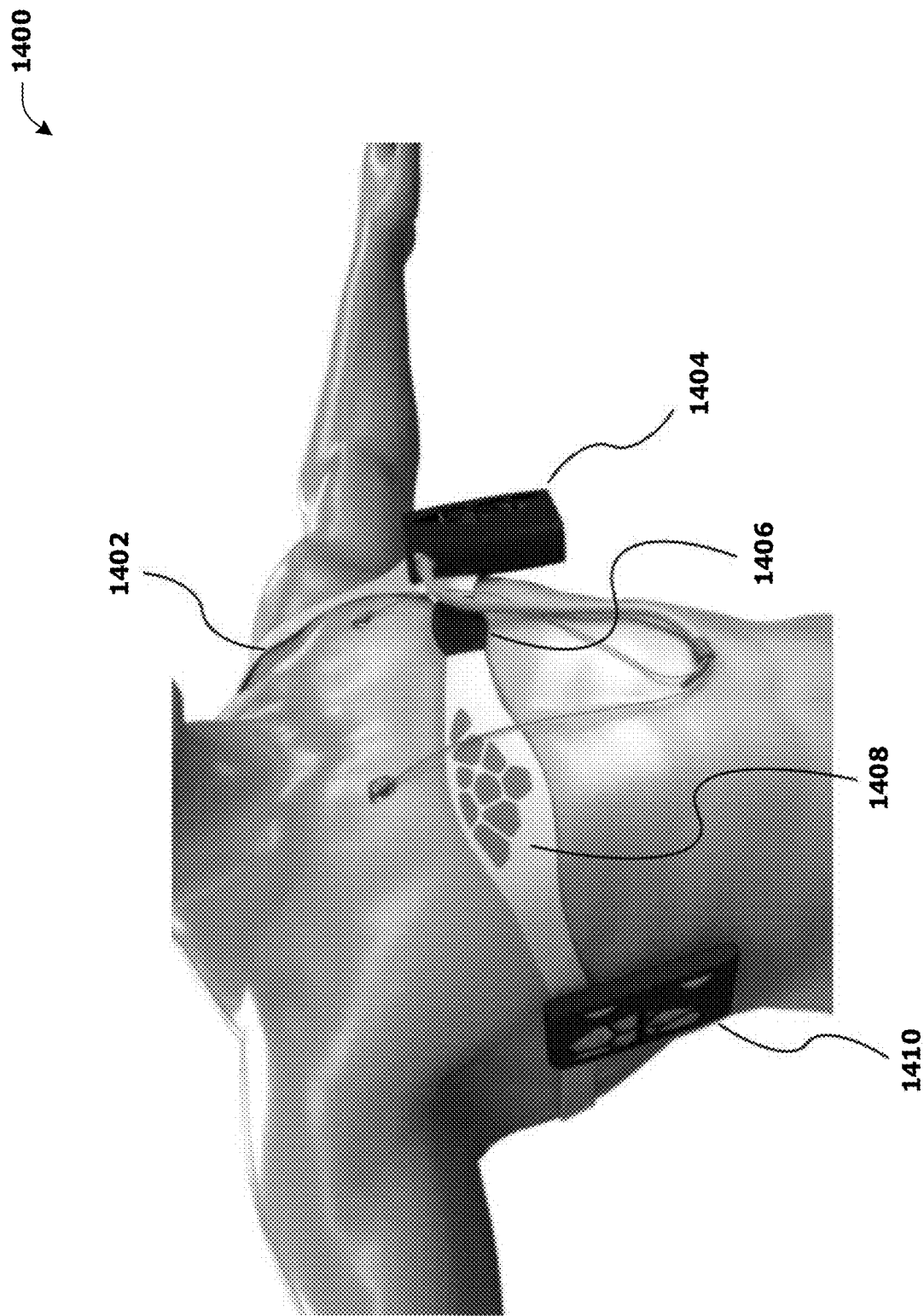
FIG. 14 is a drawing illustrating an exemplary cardiac assist device positioned on a body.

FIG. 14 illustrates a view 1400 of the cardiac assist device 100 positioned on the body. For example, the controller 808 of the cardiac assist device 100 may be placed within a first compartment 1404. Alternatively and/or additionally, one or more extra batteries may be placed in a second compartment 1410. In some examples, the first compartment 1404 and/or the second compartment 1410 may be mounted onto a band 1408. For example, the band 1408 may be wrapped around a portion of the body (e.g., the band 1408 may be wrapped around a chest area of the body). For example, a size of the band 1408 may be adjusted to be secured to the body using a clasp 1406. Alternatively and/or additionally, the band 1408 may be further secured to the body using a strap 1402 that may be mounted over a shoulder of the body. In some examples, the band 1408 may enable the person to carry accessories associated with the cardiac assist device 100, exercise, socialize with others, perform various tasks and/or activities, etc. without difficulty. Further, the band 1408 and/or the cardiac assist device 100 may not be visible to others through clothing of the person.

It may be appreciated that implementation of various embodiments of the cardiac assist device 100 presented herein may lead to benefits, such as improving patient tolerance and/or preventing death of patients waiting for a heart transplantation, treating heart failure patients long-term, the cardiac assist device 100 may be used as an alternative to VADs for patients who have contraindications to taking anticoagulants, the cardiac assist device 100 may be used as an alternative to VADs for patients showing side effects of anticoagulants, enabling patients to exercise, socialize with others, perform various tasks and/or activities, etc. without difficulty, the cardiac assist device 100 may be used by patients with heart surgery where it is not possible to separate cardiopulmonary bypass after the heart surgery, the cardiac assist device 100 doesn't have direct contact with blood (and/or has minimal direct contact with blood), there is no need to use anticoagulants, the cardiac assist device 100 is devoid of brain and pulmonary embolism, there are no brain complications, there is no need to hemolysis, left and right ventricles are both supported, risk of infection is decreased, malfunction risk is lowered, absence of mechanical components, absence of motor components (if the pump, rather than the motor, is used), low energy consumption, portability, minimal visibility through clothing, rapid (quick) implantation in the body, etc.

Figure 15:
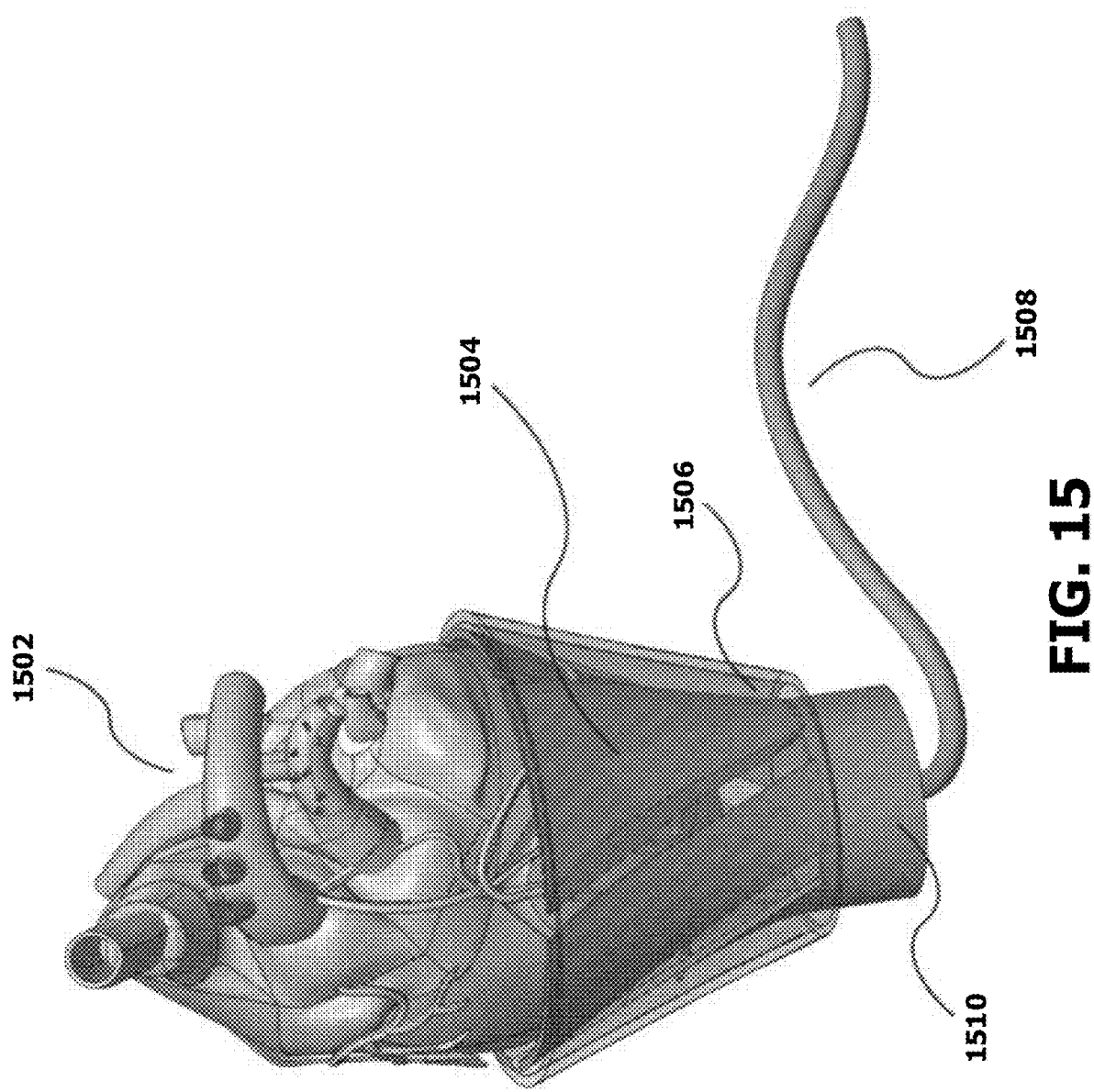
FIG. 15 is a drawing illustrating an exemplary second cardiac assist device.

FIGS. 15-19 illustrate a second cardiac assist device which may be used in place of and/or in addition to the cardiac assist device 100. FIG. 15 illustrates the second cardiac assist device. A heart 1502 is placed inside the second cardiac assist device in such a way that rotational force may be applied upon ventriculars and/or atrials that are outside (and/or inside) of the second cardiac assist device. Blades 1504 of the second cardiac assist device comprise between four and six blades (and/or a different number of blades). A number of blades of the blades 1504 may be configured based upon a heart size of the heart. The blades 1504 may have a small width at a bottom of the blades 1504 and they may become wider as they go up. There is a curve on both sides of each blade in the same direction in order not to be entangled during rotational motion of the blades. The blades 1504 may be connected to a motion generative plate 1510 (e.g., the motion generative plate 1510 may be round) from a lower side of the blades 1504. The blades 1504 may be fixed on an upper side of the motion generative plate 1510. Alternatively and/or additionally, the motion generative plate 1510 may be beside the blades 1504 and/or between the distance of ventricular and atrial. A (large) width of the blades 1504 may cause the pressure to be transferred at a wider scope to the ventricular wall and reduce damage.

The blades 1504 and the motion generative plate 1510 may be placed inside a two-layered cover 1506 in order to avoid direct contact between mechanical and rotational parts and the heart and surrounding parts. The two-layered cover 1506 may be made of silicone and/or non-sticky material to body tissues and inside the two-layered cover 1506 may be covered with a layer (e.g., coating) of hydrogel. The two-layered cover 1506 may have a shape of a cup in which the heart is placed.

The motion generative plate 1510 may connect to a lower section of the blades. The motion generative plate 1510 may cause a twist motion by creating a rotational motion of 15 to 20 degrees and transferring it to the blades 1504. Momentum that may cause the motion generative plate 1510 to rotate may be hydraulic, pneumatic and/or electrical.

A cannula 1508 is connected to lower parts of the motion generative plate 1510 through which the motion generative plate 1510 is connected to an energy source (e.g., a hydraulic, pneumatic and/or electrical energy source) outside the body which can be an electric battery and/or a pneumatic motor. The cannula 1508 may be made of polytetrafluoroethylene (PTFE).

FIG. 16 illustrates an overhead view of the second cardiac assist device. For example, a first state 1602 of the second cardiac assist device may correspond to a resting state. The blades 1504 may be separated from each other in the first state 1602 where a diastolic phase of the heart is apparent. The twist motion may occur, corresponding to a second state 1604 of the second cardiac assist device. For example, the blades 1504 may rotate around 15 degrees and/or an inner portion of the second cardiac assist device may be less apparent than in the first state 1602. In some examples, the blades 1504 may be closer to each other in the second state 1604 than in the first state 1602. Further, the blades 1504 may be closer to a center of the blades 1504 in the second state 1604 than in the first state 1602.

Figure 17:
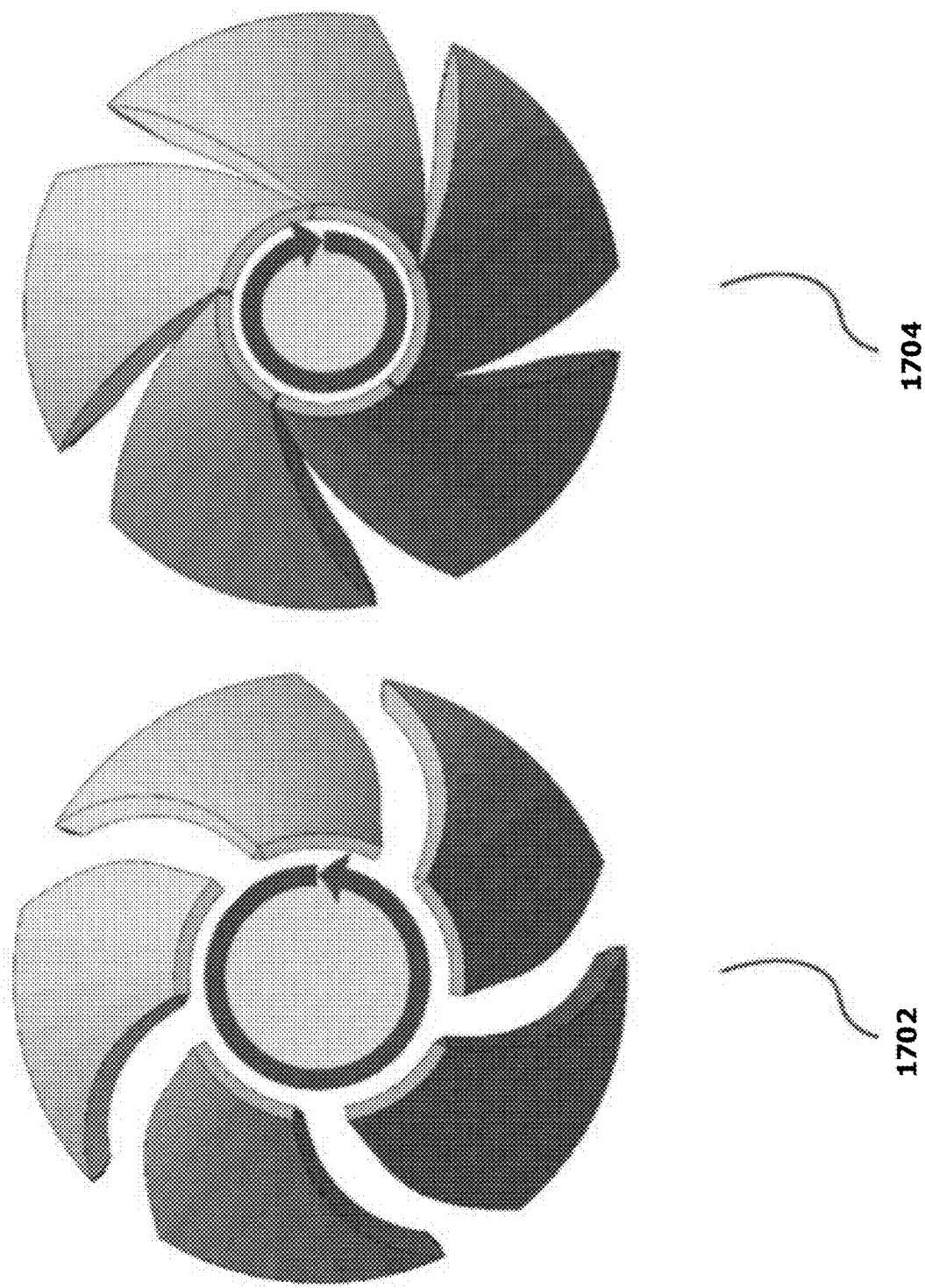
FIG. 17 is a drawing illustrating a cross sectional view of an exemplary second cardiac assist device.

FIG. 17 illustrates a cross sectional view of the second cardiac assist device. For example, the cross sectional view may be a perspective from beneath the second cardiac assist device. For example, a third state 1702 of the second cardiac assist device may correspond to the resting state. In the third state 1702, the blades 1504 may be separated from each other. The twist motion may occur, corresponding to a fourth state 1704 of the second cardiac assist device. For example, the blades 1504 may rotate around 15 degrees. In some examples, the blades 1504 may be closer to each other in the fourth state 1704 than in the third state 1702. Further, the blades 1504 may be closer to the center of the blades 1504 in the fourth state 1704 than in the third state 1702.

Figure 18:
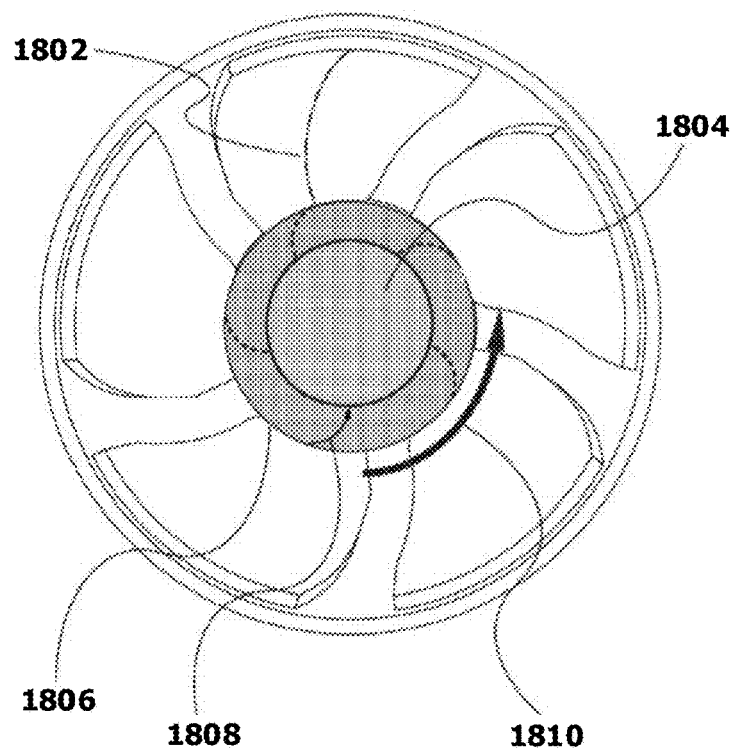
FIG. 18 is a drawing illustrating blades of an exemplary cardiac assist device.

FIG. 18 illustrates a first view of the blades 1504 of the second cardiac assist device. For example, a midline 1802 of the blades 1504 may move on the motion generative plate 1510. Alternatively and/or additionally, the blades 1504 may be at a first position 1808 of the blades 1504 when the blades 1504 are separated from each other. Alternatively and/or additionally, responsive to the twist motion, the blades 1504 may move to a second position 1804 of the blades via a motion path 1808. For example, the blades 1504 may rotate in a spiral motion direction 1810 (e.g., anti-clockwise) associated with the twist motion.

Figure 19:
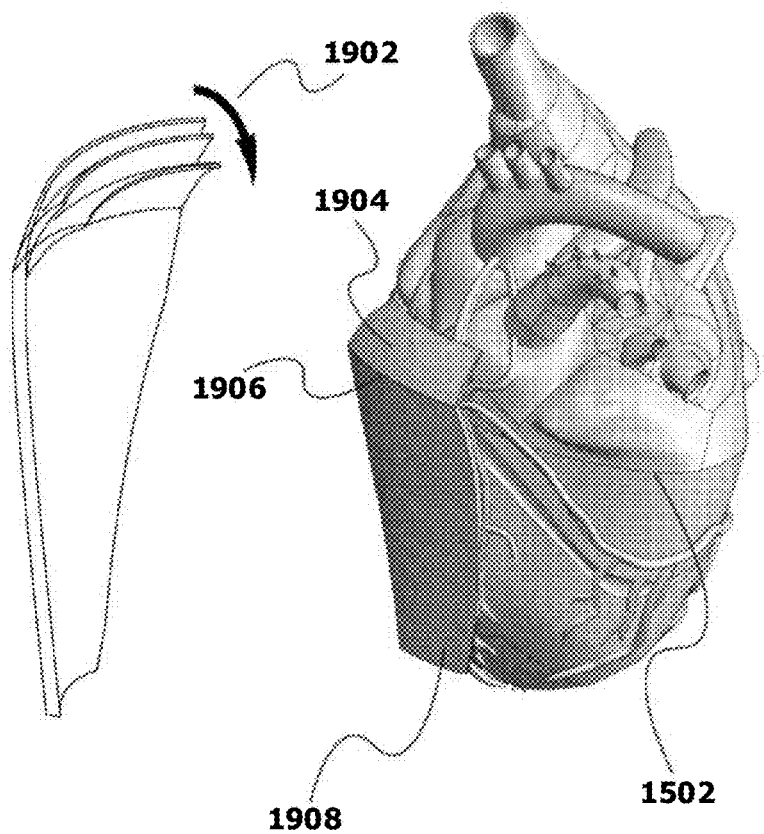
FIG. 19 is a drawing illustrating blades of an exemplary cardiac assist device.

FIG. 19 illustrates a second view of the blades 1504. A lower part of a blade 1908 is placed on a ventricle curvature and rotational force is applied to the heart to cause twisting motion. The lower part of the blade 1908 is firm and is made of compressed carbon and/or metal. An upper part of the blade 1904 is flexible and after it is bended on the atrial, it may be fitted and/or fixed on a heart ventricular to avoid the upper part of the blade 1904 moving (into the heart 1502) while the lower part of the blade 1908 moves. The upper part of the blade 1904 may be made of material that is flexible and/or formable. The upper part of the blade 1904 may be installed on an upper portion 1906 of the lower part of a blade 1908. The upper portion 1906 may be adjacent to an intersection of atrials and ventricles of the heart 1502. The upper part of the blade 1904 may be bended downwards onto the heart 1502, in a motion 1902, in order to secure the blade(s) to the heart 1502.

In some examples, the second cardiac assist device may be designed such that contact with blood of the body is minimal. Alternatively and/or additionally, the second cardiac assist device may be designed having an intracorporeal energy system.

Unless specified otherwise, "first," "second," and/or the like are not intended to imply a temporal aspect, a spatial aspect, an ordering, etc. Rather, such terms are merely used as identifiers, names, etc. for features, elements, items, etc. For example, a first object and a second object generally correspond to object A and object B or two different or two identical objects or the same object.

Moreover, "example" is used herein to mean serving as an instance, illustration, etc., and not necessarily as advantageous. As used herein, "or" is intended to mean an inclusive "or" rather than an exclusive "or". In addition, "a" and "an" as used in this application are generally be construed to mean "one or more" unless specified otherwise or clear from context to be directed to a singular form. Also, at least one of A and B and/or the like generally means A or B or both A and B. Furthermore, to the extent that "includes", "having", "has", "with", and/or variants thereof are used in either the detailed description or the claims, such terms are intended to be inclusive in a manner similar to the term "comprising".

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing at least some of the claims.

Various operations of embodiments and/or examples are provided herein. The order in which some or all of the operations are described herein should not be construed as to imply that these operations are necessarily order dependent. Alternative ordering will be appreciated by one skilled in the art having the benefit of this description. Further, it will be understood that not all operations are necessarily present in each embodiment and/or example provided herein. Also, it will be understood that not all operations are necessary in some embodiments and/or examples.

Also, although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure. In addition, while a particular feature of the disclosure may have been disclosed with respect to only one of several implementations, such feature may be combined with one or more other features of the other implementations as may be desired and advantageous for any given or particular application.

What is claimed is:

1. A cardiac assist device, comprising:
a structure surrounding at least a portion of a heart, wherein the structure comprises:
a first ring on a first side of the structure;
a second ring on a second side of the structure; and
a plurality of columns connecting the first ring to the second ring;
an inner cup enclosing at least a portion of the structure;
an outer cup enclosing at least a portion of the inner cup, wherein; the outer cup comprises an opening; and
a pump, wherein the pump is configured to:
conduct gas into a space between the outer cup and the inner cup via the opening of the outer cup, wherein the conduction of the gas into the space between the outer cup and the inner cup causes a first motion of the structure comprising a first rotation of the second ring in a first direction; and
conduct the gas from the space between the outer cup and the inner cup to outside of the outer cup via the opening of the outer cup, wherein the conduction of the gas from the space between the outer cup and the inner cup to the outside of the outer cup causes a second motion of the structure comprising a second rotation of the second ring in a second direction, different than the first direction.

2. The cardiac assist device of claim 1, comprising:
one or more sensors configured to detect one or more measurements associated with the heart; and
a controller configured to control the pump based upon the one or more measurements.

3. The cardiac assist device of claim 2, wherein:
the pump is configured to conduct the gas into the space between the outer cup and the inner cup and to conduct the gas from the space between the outer cup and the inner cup to the outside of the outer cup periodically, at a rate;
the one or more measurements comprise a heart rate measurement of the heart; and
the rate is controlled based upon the heart rate measurement.

4. The cardiac assist device of claim 1, wherein:
the inner cup comprises a plurality of layers; and
the structure is positioned between a first layer of the plurality of layers and a second layer of the plurality of layers.

5. The cardiac assist device of claim 1, wherein:
each column of the plurality of columns comprises a first curvature at a first point of the column and a second curvature at a second point of the column.

6. The cardiac assist device of claim 1, wherein:
the first motion of the structure is a first twisting motion of the structure in the first direction;
the second motion of the structure is a second twisting motion of the structure in the second direction; and
the first motion and the second motion increase pumping power of the heart.

7. The cardiac assist device of claim 1, wherein:
the first ring surrounds a first portion of the heart;
the second ring is adjacent to a bottom the heart;
the first rotation of the second ring in the first direction is between 15 to 20 degrees; and
the second rotation of the second ring in the second direction is between 15 to 20 degrees.

8. The cardiac assist device of claim 1, wherein at least one of the first ring, the outer cup or the inner cup is configured to be sutured to a pericardium of the heart.

9. The cardiac assist device of claim 1, wherein:
the outer cup is made of a first silicone-based material;
the inner cup is made of a second silicone-based material; and
the structure is made of a plastic.

10. The cardiac assist device of claim 1, wherein:
the outer cup has a first level of flexibility;
the inner cup has a second level of flexibility;
the structure has a third level of flexibility;
the second level of flexibility is higher than the first level of flexibility; and
the third level of flexibility is higher than the first level of flexibility.

11. The cardiac assist device of claim 1, comprising:
a cannula connected to the opening, wherein the pump is configured to:
conduct the gas into the space between the outer cup and the inner cup via the cannula and the opening of the outer cup; and
conduct the gas from the space between the outer cup and the inner cup to outside of the outer cup via the cannula and the opening of the outer cup.

12. The cardiac assist device of claim 1, wherein:
a part of the outer cup is connected to a part of the inner cup, wherein the connection between the part of the outer cup and the part of the inner cup is configured to seal the space between the outer cup and the inner cup.

13. A cardiac assist device, comprising:
a structure surrounding at least a portion of a heart, wherein the structure comprises:
a first ring on a first side of the structure;
a second ring on a second side of the structure; and
a plurality of columns connecting the first ring to the second ring;
an inner cup comprising a plurality of layers, wherein the structure is positioned between a first layer of the plurality of layers and a second layer of the plurality of layers;
an outer cup enclosing at least a portion of the inner cup, wherein the outer cup comprises an opening; and
a pump, wherein the pump is configured to:
conduct gas into a space between the outer cup and the inner cup via the opening of the outer cup, wherein the conduction of the gas into the space between the outer cup and the inner cup causes a first motion of the structure comprising a first rotation of the second ring in a first direction; and
conduct the gas from the space between the outer cup and the inner cup to outside of the outer cup via the opening of the outer cup, wherein the conduction of the gas from the space between the outer cup and the inner cup to the outside of the outer cup causes a second motion of the structure comprising a second rotation of the second ring in a second direction, different than the first direction.

14. The cardiac assist device of claim 13, comprising:
a cannula connected to the opening, wherein the pump is configured to:
conduct the gas into the space between the outer cup and the inner cup via the cannula and the opening of the outer cup; and
conduct the gas from the space between the outer cup and the inner cup to outside of the outer cup via the cannula and the opening of the outer cup.

15. The cardiac assist device of claim 13, wherein:
a part of the outer cup is connected to a part of the inner cup, wherein the connection between the part of the outer cup and the part of the inner cup is configured to seal the space between the outer cup and the inner cup.

16. A cardiac assist device, comprising:
a structure surrounding at least a portion of a heart, wherein the structure comprises:
   a first ring on a first side of the structure;
   a second ring on a second side of the structure; and
   a plurality of columns connecting the first ring to the second ring;
an inner cup comprising a plurality of layers, wherein the structure is positioned between a first layer of the plurality of layers and a second layer of the plurality of layers;
an outer cup enclosing at least a portion of the inner cup, wherein the outer cup comprises an opening;
a cannula connected to the opening; and
a pump, wherein the pump is configured to:
   conduct gas into a space between the outer cup and the inner cup via the cannula and the opening of the outer cup, wherein the conduction of the gas into the space between the outer cup and the inner cup causes a first motion of the structure comprising a first rotation of the second ring in a first direction; and
   conduct the gas from the space between the outer cup and the inner cup to outside of the outer cup via the cannula and the opening of the outer cup, wherein the conduction of the gas from the space between the outer cup and the inner cup to the outside of the outer cup causes a second motion of the structure comprising a second rotation of the second ring in a second direction, different than the first direction, wherein a part of the outer cup is connected to a part of the inner cup, wherein the connection between the part of the outer cup and the part of the inner cup is configured to seal the space between the outer cup and the inner cup.

\* \* \* \* \*